United States Patent
McSweeney et al.

(10) Patent No.: US 12,361,821 B2
(45) Date of Patent: Jul. 15, 2025

(54) CONTINUOUS PATIENT MONITORING

(71) Applicant: Welch Allyn, Inc., Skaneateles Falls, NY (US)

(72) Inventors: WonKyung McSweeney, Manlius, NY (US); Stacey A. Fitzgibbons, Dewitt, NY (US); Thomas A. Gurgol, Clay, NY (US); David L. Kellner, Baldwinsville, NY (US); Christopher L. Long, Chittenango, NY (US); Rebecca Quilty-Koval, Baldwinsville, NY (US); Ching Yue Yeung, Fayetteville, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 289 days.

(21) Appl. No.: 17/820,443

(22) Filed: Aug. 17, 2022

(65) Prior Publication Data

US 2023/0063782 A1  Mar. 2, 2023

Related U.S. Application Data

(60) Provisional application No. 63/237,758, filed on Aug. 27, 2021.

(51) Int. Cl.
*G08B 29/26* (2006.01)
*G08B 21/18* (2006.01)

(52) U.S. Cl.
CPC ............. *G08B 29/26* (2013.01); *G08B 21/18* (2013.01)

(58) Field of Classification Search
CPC ................................. G08B 29/26; G08B 21/18
See application file for complete search history.

(56) References Cited

U.S. PATENT DOCUMENTS

| | | | |
|---|---|---|---|
| 5,438,983 A | | 8/1995 | Falcone |
| 5,724,025 A | * | 3/1998 | Tavori ............... A61B 5/1112 600/300 |
| 6,024,699 A | * | 2/2000 | Surwit ................ G16H 20/10 128/920 |
| 6,081,742 A | | 6/2000 | Amano et al. |
| 6,241,661 B1 | | 6/2001 | Schluess et al. |
| 6,890,304 B1 | * | 5/2005 | Amano ............... A61B 5/4854 606/65 |

(Continued)

FOREIGN PATENT DOCUMENTS

| | | |
|---|---|---|
| WO | 2011116340 A2 | 9/2011 |
| WO | 2014140978 A1 | 9/2014 |

(Continued)

OTHER PUBLICATIONS

Extended European Search Report for Application No. 22192115.8 mailed Jan. 5, 2023.

*Primary Examiner* — Steven Lim
*Assistant Examiner* — Son M Tang
(74) *Attorney, Agent, or Firm* — Merchant & Gould P.C.

(57) ABSTRACT

A device for monitoring a physiological variable determines a starting value for a self-adjusting alarm limit based on an abnormal state of the physiological variable. The device determines a new value for the self-adjusting alarm limit from physiological data values received during a time window. When the new value for the self-adjusting alarm limit moves in a targeted direction, the device resets the self-adjusting alarm limit at the new value.

19 Claims, 15 Drawing Sheets

(56) References Cited

U.S. PATENT DOCUMENTS

| | | | |
|---|---|---|---|
| 7,052,472 B1 | 5/2006 | Miller | |
| 7,066,883 B2 * | 6/2006 | Schmidt | G16H 40/67 |
| | | | 128/920 |
| 8,028,694 B2 | 10/2011 | Hickle | |
| 8,275,553 B2 * | 9/2012 | Ochs | A61B 5/4818 |
| | | | 702/19 |
| 8,690,771 B2 * | 4/2014 | Wekell | G16H 15/00 |
| | | | 705/2 |
| 8,956,292 B2 | 2/2015 | Wekell et al. | |
| 9,636,056 B2 | 5/2017 | Al-Ali | |
| 9,636,070 B2 | 5/2017 | Kassem et al. | |
| 9,724,024 B2 * | 8/2017 | Al-Ali | A61B 5/1455 |
| 9,867,575 B2 | 1/2018 | Maani et al. | |
| 10,052,072 B2 | 8/2018 | Tsugo | |
| 10,098,591 B2 | 10/2018 | Al-Ali et al. | |
| 10,264,982 B2 | 4/2019 | Ahmed et al. | |
| 10,265,030 B2 | 4/2019 | Johnson et al. | |
| 10,485,488 B2 | 11/2019 | Bhat et al. | |
| 10,638,937 B2 | 5/2020 | Ma et al. | |
| 10,674,938 B2 | 6/2020 | Perez De Alejo Fortun | |
| 10,702,174 B2 | 7/2020 | Fasciano | |
| 10,827,961 B1 * | 11/2020 | Iyengar | A61B 5/1455 |
| 10,891,766 B1 | 1/2021 | Gough et al. | |
| 10,925,522 B2 * | 2/2021 | Chang | A61B 5/0022 |
| 10,976,908 B2 | 4/2021 | Freeman et al. | |
| 2002/0169366 A1 * | 11/2002 | Schmidt | G16H 40/67 |
| | | | 128/920 |
| 2004/0230105 A1 * | 11/2004 | Geva | A61B 5/316 |
| | | | 600/509 |
| 2005/0010447 A1 | 1/2005 | Miyasaka et al. | |
| 2005/0177096 A1 | 8/2005 | Bollish et al. | |
| 2007/0232867 A1 * | 10/2007 | Hansmann | G16H 40/67 |
| | | | 600/300 |
| 2008/0086035 A1 * | 4/2008 | Messerges | A61B 5/4821 |
| | | | 600/300 |
| 2009/0043182 A1 * | 2/2009 | Brauker | A61B 5/145 |
| | | | 600/347 |
| 2009/0210163 A1 * | 8/2009 | Ochs | A61B 5/4818 |
| | | | 702/19 |
| 2011/0213212 A1 * | 9/2011 | Al-Ali | G08B 29/26 |
| | | | 600/300 |
| 2011/0245688 A1 | 10/2011 | Arora | |
| 2011/0301436 A1 * | 12/2011 | Teixeira | A61B 5/14552 |
| | | | 702/19 |
| 2012/0016255 A1 | 1/2012 | Masuo | |
| 2012/0116194 A1 * | 5/2012 | Gross | G16H 20/10 |
| | | | 600/323 |
| 2012/0277545 A1 * | 11/2012 | Teixeira | G16H 50/50 |
| | | | 600/301 |
| 2012/0330565 A1 * | 12/2012 | Ochs | A61B 5/316 |
| | | | 702/19 |
| 2014/0266786 A1 * | 9/2014 | Sugiyama | A61B 5/742 |
| | | | 340/870.4 |
| 2015/0077268 A1 | 3/2015 | Lane et al. | |
| 2016/0155309 A1 * | 6/2016 | Watson | A61B 5/7282 |
| | | | 600/324 |
| 2016/0163187 A1 * | 6/2016 | Treacy | A61B 5/7282 |
| | | | 340/501 |
| 2016/0220197 A1 | 8/2016 | Rantala | |
| 2017/0202469 A1 | 7/2017 | Scharf et al. | |
| 2017/0225336 A1 * | 8/2017 | Deyle | B25J 11/008 |
| 2018/0078219 A1 * | 3/2018 | Selvaraj | A61B 5/7221 |
| 2019/0142343 A1 | 5/2019 | Emmons et al. | |
| 2019/0164633 A1 | 5/2019 | Ingel et al. | |
| 2019/0183354 A1 | 6/2019 | Rowe | |
| 2019/0246966 A1 * | 8/2019 | Friedman | A61B 5/366 |
| 2020/0121199 A1 | 4/2020 | Freeman et al. | |
| 2020/0261009 A1 * | 8/2020 | Everman | G01P 13/00 |
| 2020/0273581 A1 * | 8/2020 | Wolf | G16H 40/63 |
| 2020/0335190 A1 | 10/2020 | Chung et al. | |
| 2021/0015425 A1 | 1/2021 | Clift-Reaves et al. | |
| 2023/0190209 A1 * | 6/2023 | McSweeney | G08B 21/182 |
| | | | 340/539.12 |

FOREIGN PATENT DOCUMENTS

| | | |
|---|---|---|
| WO | 2017221745 A1 | 12/2017 |
| WO | 2020197903 A1 | 1/2020 |

* cited by examiner

CONTINUOUS PATIENT MONITORING

BACKGROUND

During continuous patient monitoring, an alarm is often set with a pair of upper and lower alarm limits. The alarm is triggered when a patient's monitored vital signs are below the lower alarm limit, or when the patient's vital signs are above the upper alarm limit.

When the patient's vital signs are improving or deteriorating, an alarm is often manually reset according to newly established baselines for the patient. This requires additional action from clinicians, which can be labor-intensive and time consuming. When an alarm is not appropriately reset, often the alarm is repeatedly triggered, which can lead to alarm fatigue.

Additionally, clinicians are often unable to determine whether an alarm is triggered due to patient deterioration, or due to administered medications, treatments, and noise artifacts. This can lead to confusion regarding the need to respond to the alarm, and further alarm fatigue.

SUMMARY

In general terms, the present disclosure relates to vital sign alarms and visualizations. In one possible configuration, a monitor device provides self-adjusting upper and lower alarm limits that can more accurately monitor a patient's measured vital signs, and reduce alarm fatigue. The monitor device can further provide enhanced visualization of the measured vital signs that can boost confidence in their accuracy, and help aid clinicians make decisions such as whether to intervene or adjust one or more alarm settings. Various vital signs can be monitored in accordance with implementations of the present disclosure. For instance, at least one of heart rate, blood pressure, blood oxygen saturation percentage, respiration rate, electrocardiogram, and end tidal carbon dioxide (etCO2) can be monitored. Various aspects are described in this disclosure, which include, but are not limited to, the following aspects.

In one aspect, a device for monitoring a physiological variable comprises: at least one processing device; and a memory device storing instructions which, when executed by the at least one processing device, cause the device to: determine a starting value for a self-adjusting alarm limit based on an abnormal state of the physiological variable; determine a new value for the self-adjusting alarm limit from physiological data values received during a time window; and when the new value for the self-adjusting alarm limit moves in a targeted direction, reset the self-adjusting alarm limit at the new value.

In another aspect, a method of continuous physiological monitoring comprises: determining a starting value for a self-adjusting alarm limit based on an abnormal state of the physiological variable; determining a new value for the self-adjusting alarm limit from physiological data values received during a time window; resetting the self-adjusting alarm limit at the new value when the new value for the self-adjusting alarm limit moves in a targeted direction; and triggering an alarm when the new value for the self-adjusting alarm limit moves in a direction opposite of the targeted direction.

In another aspect, a device for monitoring a physiological variable comprises: at least one processing device; and a memory device storing instructions which, when executed by the at least one processing device, cause the device to: receive physiological data values from a physiological sensor; receive artifact data including audio signals captured from an audio sensor; process the audio signals to determine one or more artifacts; and display the physiological data values to distinguish values effected by the one or more artifacts from values not effected by the one or more artifacts.

In another aspect, a device for monitoring a physiological variable comprises: at least one processing device; and a memory device storing instructions which, when executed by the at least one processing device, cause the device to: receive physiological data values from a physiological sensor; receive a treatment event; determine an expected effect of the treatment event on the physiological data values, the expected effect being a targeted effect or a side effect; display the treatment event overlayed on the physiological data values; display a normal range overlayed on the physiological data values, the normal range having a first set of upper and lower limits; and display a modified range overlayed over the physiological data values, the modified range having a second set of upper and lower limits that are based on the expected effect of the treatment event.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
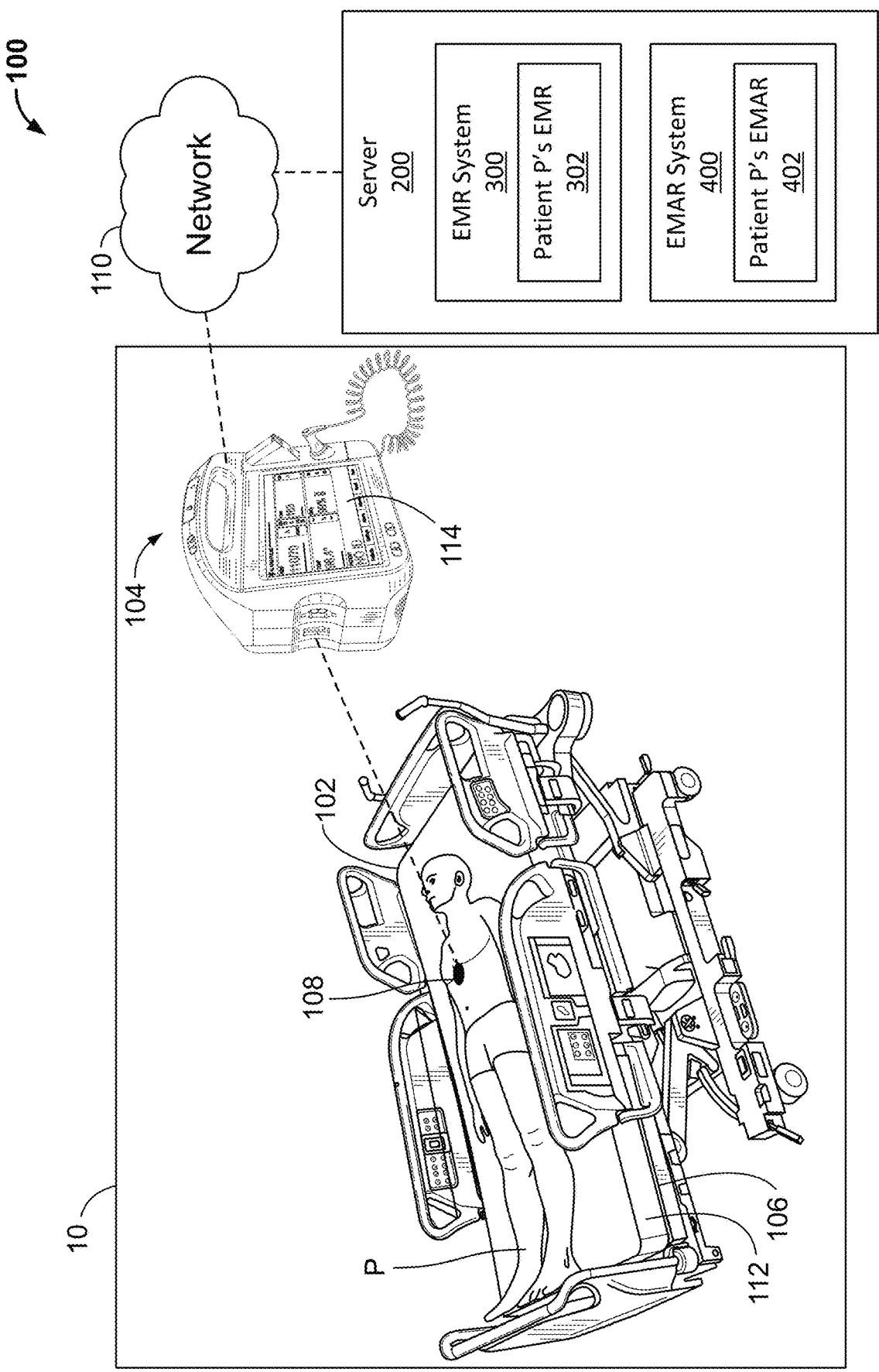
FIG. 1 illustrates an example of a monitoring system for monitoring vital signs of a patient who is shown resting on a patient support system.

FIG. 1 illustrates an example of a monitoring system 100 for monitoring vital signs of a patient P who is shown resting on a patient support system 102. The monitoring system 100 includes the patient support system 102, as well as a monitor device 104, a motion sensor 106, and a physiological sensor 108, which are all shown inside an area 10. In some examples, the area 10 is a patient room, a pre-operative or post-operative holding area, an operating room, a waiting room, or other type of area within a healthcare facility such as a hospital, a surgical center, a nursing home, a long term care facility, or similar type of facility.

The patient P is a person, such as a patient, who is being clinically treated by one or more clinicians in the area 10. Examples of clinicians include primary care providers (e.g., doctors, nurse practitioners, and physician assistants), nursing care providers (e.g., nurses), specialty care providers (e.g., professionals in various specialties), and health professionals that provide preventive, curative, promotional and rehabilitative health care services.

In the example shown in FIG. 1, the patient support system 102 is a hospital bed. In other examples, the patient support system 102 is another type of bed, lift, chair, wheelchair, stretcher, surgical table, and the like, which can support the patient P in the area 10.

The monitor device 104 is connected to the physiological sensor 108, and includes a display device 114 for displaying physiological data acquired from the physiological sensor 108. The physiological sensor 108 communicates wirelessly or via wired connection with the monitor device 104. The monitor device 104 may also communicate with one or more additional sensing devices in the area 10, including the patient support system 102 and the motion sensor 106.

The monitor device 104 may be any suitable type of monitoring device. FIG. 1 illustrates the monitor device 104 as a multi-parameter device which displays multiple parameters on the display device 114. The multiple parameters are detected from the physiological sensor 108 and from other sensing devices inside the area 10. In alternative examples, the monitor device 104 may be a single-parameter device, such as an ECG monitor.

Examples of the physiological sensor 108 include an electrocardiogram (ECG) sensor, a blood oxygen saturation/pulse oximeter (SpO2) sensor, a blood pressure sensor, a heart rate sensor, a respiration rate sensor, an end tidal carbon dioxide (etCO2) sensor, and the like. The physiological sensor 108 can also combine two or more sensors in a single sensor device.

As shown in FIG. 1, the monitor device 104 communicates with a server 200 via a communications network 110. The server 200 operates to manage the patient P's medical history and information. The server 200 can be operated by a healthcare service provider, such as a hospital or medical clinic. The monitor device 104 sends physiological data acquired from the physiological sensor 108 to the server 200 via the connection to the communications network 110. In at least some examples, the server 200 is a cloud server or similar type of server.

The server 200 can include an electronic medical record (EMR) system 300 (alternatively termed electronic health record (EHR)). Advantageously, the server 200 can automatically store the physiological data acquired from the monitor device 104 in an electronic medical record 302 or electronic health record of the patient P located in the EMR system 300 via the connection with the monitor device 104 over the communications network 110.

The server 200 can also include an electronic medication administration records (EMAR) system 400. The monitor device 104 can communicate with the EMAR system 400 via the connection to the communications network 110 to obtain access to a medication record 402 of the patient P that includes medications and time stamps when administered to the patient P.

In the example shown in FIG. 1, the motion sensor 106 is a motion sensor positioned below, within, or on top of a mattress 112 of the patient support system 102. The motion sensor 106 can include piezoelectric sensors, load cells, or combinations thereof that detect movements of the patient P while the patient P is supported on the patient support system 102.

In alternative examples, the motion sensor 106 may be an accelerometer attached to the patient P, or incorporated into the physiological sensor 108 and/or into one or more other sensing devices that are attached to the patient P. In such examples, physiological sensing and motion detection functions are combined in one device. Multiple such devices may be used on the patient P. For example, a combined ECG/motion detection device and/or a combined pulse oximetry/motion detection device may be used on the patient P at the same time.

The motion sensor 106 detects motion by the patient P, which can affect or influence the heart rate, blood pressure, and respiration rate data sensed by the physiological sensor 108. The motion sensor 106 senses motion by the patient P (for example by using piezoelectric or load cell sensors positioned below, within, or on top of a mattress 112 or accelerometers attached to the patient P), and transmits the sensed motion data to the monitor device 104 while the physiological sensor 108 senses physiological data such as the heart rate, blood pressure, or respiration rate of the patient P, and transmits the physiological data to the monitor device 104.

The monitor device 104 processes the data from the motion sensor 106 to identify when the patient P is moving. The monitor device 104 can then flag the physiological data that was measured when the patient P was moving. For example, the monitor device 104 can display the physiological data that was acquired when the patient P was moving differently from when the patient P was not moving to aid a clinician's assessment of the patient P.

The communications network 110 communicates data between one or more devices, such as between the monitor device 104 and the server 200. In some examples, the communications network 110 may also be used to communicate data between one or more devices inside the area 10 such as between the patient support system 102, monitor device 104, motion sensor 106, physiological sensor 108, and other sensor devices inside the area 10.

The communications network 110 can include any type of wired or wireless connections or any combinations thereof. Examples of wireless connections include broadband cellular network connections such as 4G or 5G. In some examples, wireless connections are also accomplished using Wi-Fi, ultra-wideband (UWB), Bluetooth, radio frequency identification (RFID), and similar types of wireless connections.

Figure 2:
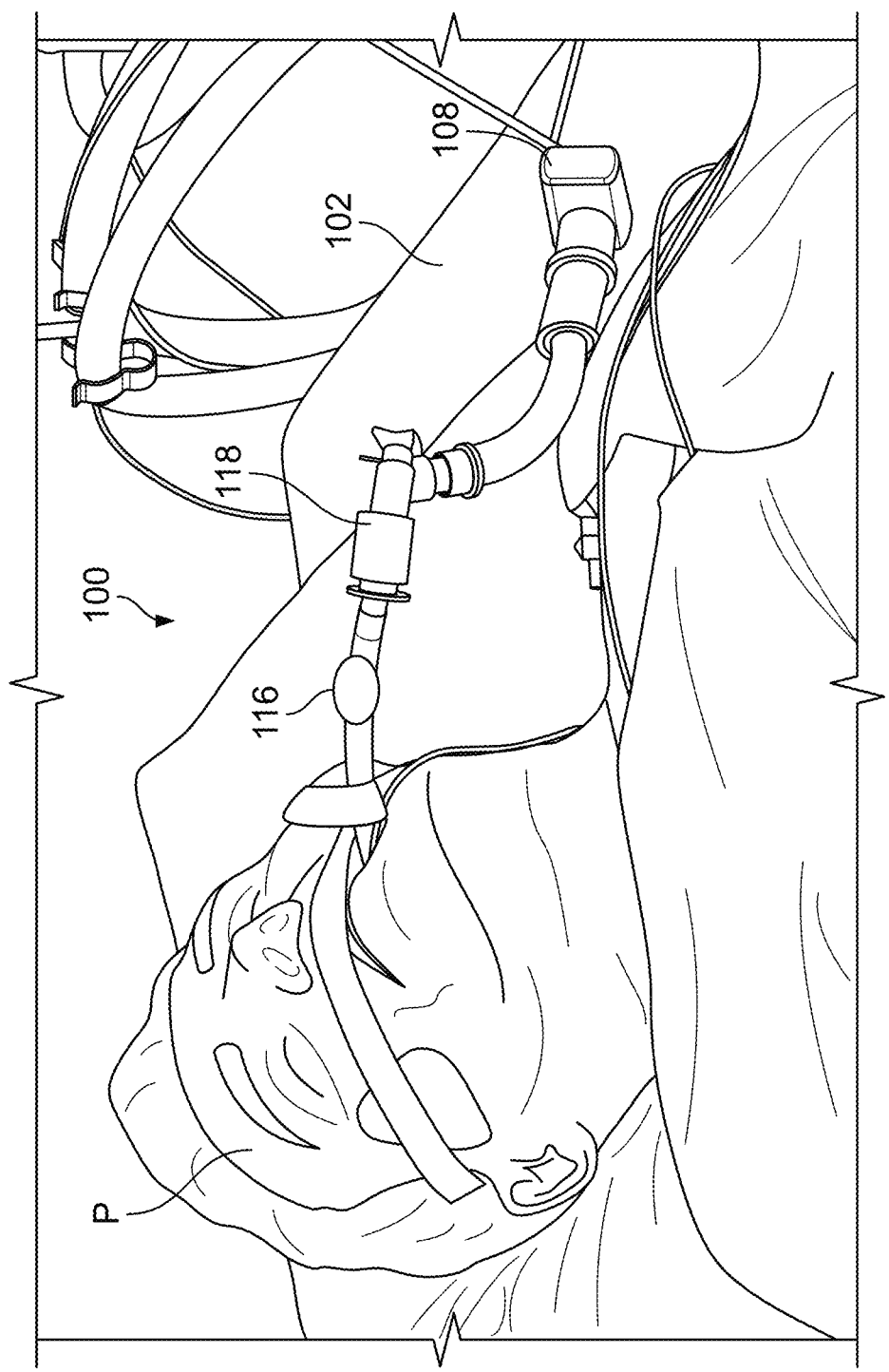
FIG. 2 illustrates an example of an audio sensor of the monitoring system of FIG. 1, the audio sensor being shown positioned close to the patient.

FIG. 2 illustrates an example of an audio sensor 116 that may also be a part of the monitoring system 100. In the example shown in FIG. 2, the audio sensor 116 is attached to an apparatus 118 connected to the patient P. The apparatus 118 can be a nasal cannula, a tracheal intubation tube, a face mask, a capnography monitor, or similar device such that the audio sensor 116 is positioned near to the patient P's mouth or chest. Alternatively, the audio sensor 116 can be attached directly to the patient P, or to another object near the patient P.

In the example shown in FIG. 2, the physiological sensor 108 is also attached to the apparatus 118. In this example, the physiological sensor 108 is a capnography sensor that can be used to measure the etCO2 and respiration rate of the patient P.

The audio sensor 116 captures audio sounds that can be used to detect when the patient P is coughing, talking, and eating, which can affect or influence the respiration rate and etCO2 data sensed by the physiological sensor 108. The audio sensor 116 captures audio data by the patient P, and transmits the audio data to the monitor device 104. Additionally, the physiological sensor 108 acquires etCO2 and respiration rate data of the patient P, and transmits the etCO2 and respiration rate data to the monitor device 104.

The monitor device 104 processes the audio data from the audio sensor 116 to identify when the patient P is coughing, talking, and eating. The monitor device 104 can then flag the etCO2 and respiration rate data that was measured when the patient P was coughing, talking, and eating. For example, the monitor device 104 can display the etCO2 and respiration rate data that was acquired during coughing, talking, or eating differently from when the patient P was not coughing, talking, or eating to aid a clinician's assessment of the patient P.

Figure 3:
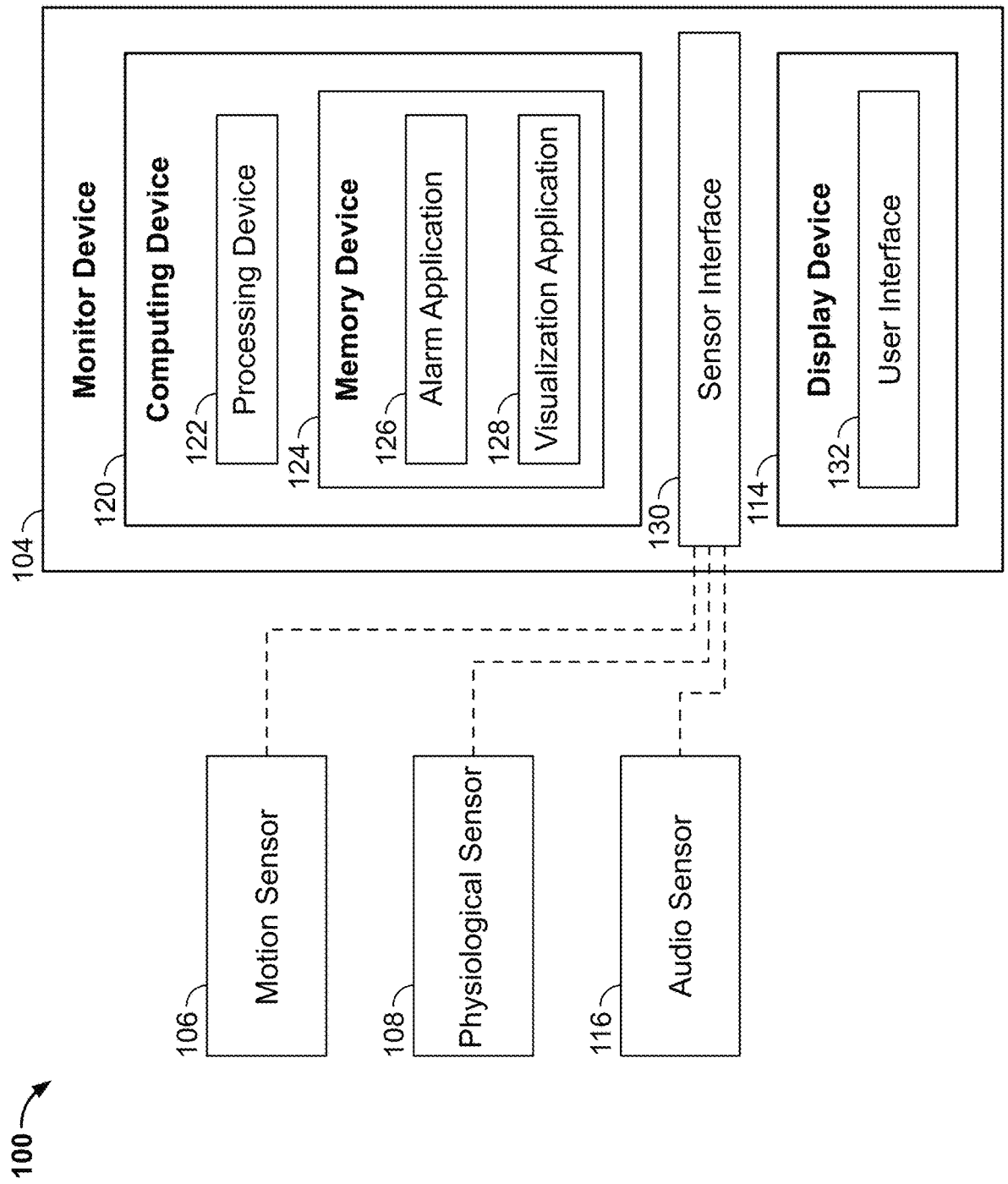
FIG. 3 schematically illustrates an example of the monitoring system of FIG. 1, which includes a monitor device, motion sensor, physiological sensor, and audio sensor.

FIG. 3 schematically illustrates an example of the monitoring system 100. The monitor device 104 includes a computing device 120 having at least one processing device 122 and a memory device 124. The at least one processing device 122 is an example of a processing unit such as a central processing unit (CPU). The at least one processing device 122 can include one or more CPUs. The at least one processing device 122 can include one or more digital signal processors, field-programmable gate arrays, or other electronic circuits.

The memory device 124 operates to store data and instructions for execution by the at least one processing device 122, including an alarm application 126 and a visualization application 128, which will both be described in more detail below. The memory device 124 includes computer-readable media, which may include any media that can be accessed by the monitor device 104. By way of example, computer-readable media include computer readable storage media and computer readable communication media.

Computer readable storage media includes volatile and nonvolatile, removable and non-removable media implemented in any device configured to store information such as computer readable instructions, data structures, program modules, or other data. Computer readable storage media can include, but is not limited to, random access memory, read only memory, electrically erasable programmable read only memory, flash memory, and other memory technology, including any medium that can be used to store information that can be accessed by the monitor device 104. The computer readable storage media is non-transitory.

Computer readable communication media embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are within the scope of computer readable media.

The monitor device 104 further includes a sensor interface 130 that operates to communicate with the various sensors of the monitoring system 100. The sensor interface 130 can include both wired interfaces and wireless interfaces. The motion sensor 106, physiological sensor 108, and audio sensor 116 can wirelessly connect to the sensor interface 130 through Wi-Fi, ultra-wideband (UWB), Bluetooth, and similar types of wireless connections. Alternatively, the motion sensor 106, physiological sensor 108, and audio sensor 116 can be connected to the monitor device 104 using wired connections that plug into the sensor interface 130.

As shown in FIG. 3, the monitor device 104 includes the display device 114, which operates to display a user interface 132. In some examples, the display device 114 is a touchscreen such that the user interface 132 operates to receive inputs from a clinician. In such examples, the display device 114 operates as both a display device and a user input device. The monitor device 104 can also support physical buttons on a housing of the device that operate to receive inputs from the clinician to control operation of the monitor device and enter data.

Figure 4:
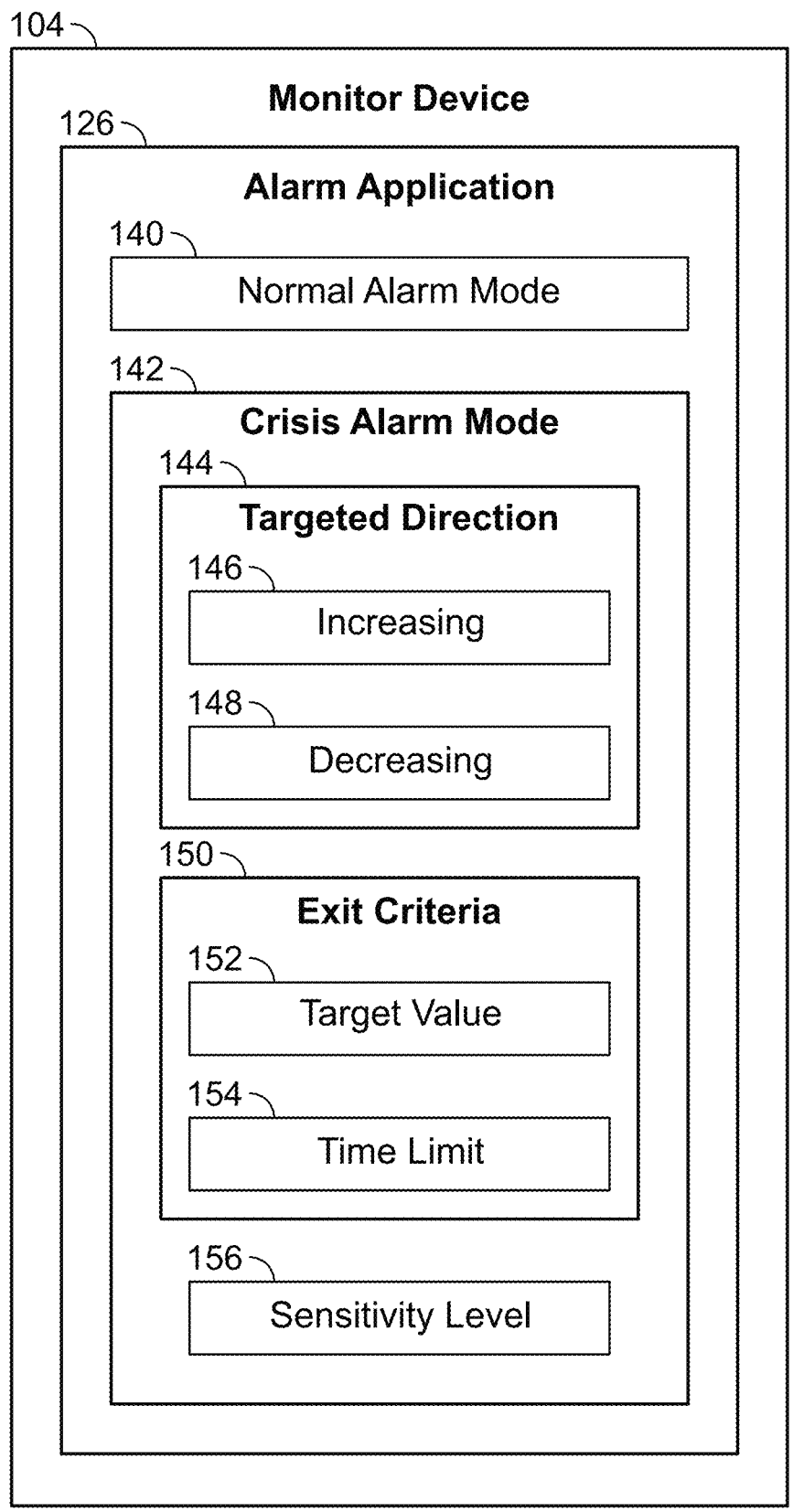
FIG. 4 schematically illustrates an example of an alarm application installed on the monitor device of FIG. 3.

FIG. 4 schematically illustrates an example of the alarm application 126 installed on the monitor device 104. The alarm application 126 includes a normal alarm mode 140 and a crisis alarm mode 142. A clinician can select either the normal alarm mode 140 or the crisis alarm mode 142 when operating the monitor device 104. When the display device 114 is a touchscreen, the clinician can select the normal alarm mode 140 or the crisis alarm mode 142 on the display device 114. Alternatively, the clinician can select one or more user input buttons on the monitor device 104 to select the normal alarm mode 140 or the crisis alarm mode 142.

The normal alarm mode 140 is a mode of operation where fixed upper and lower alarm limits are set for the physiological data sensed from the physiological sensor 108. In the normal alarm mode 140, an alarm is triggered when the physiological data is above the upper alarm limit, or is below the lower alarm limit. Illustrative examples of the alarm include a local alarm on the monitor device 104 such as a visual alarm (e.g., blinking red light) and/or an audible alarm (e.g., beeping noise), and/or may also include notifications sent to mobile devices carried by clinicians (e.g., smartphones), and/or notifications sent to a nurses' station.

In the normal alarm mode 140, the upper and lower alarm limits are based on normal or default values. As an illustrative example, a normal resting blood pressure for human adults is approximately 120/80 mmHg, a high blood pressure for human adults is considered to be 140/90 mmHg or higher, and a low blood pressure for human adults is considered to be 90/60 mmHg or lower. When monitoring the blood pressure of the patient P under the normal alarm mode 140, an upper alarm limit can be set at 140/90 mmHg and a lower alarm limit can be set at 90/60 mmHg. When the blood pressure of the patient P is above 140/90 mmHg an alarm is triggered. Also, when the blood pressure of the patient P is below 90/60 mmHg, an alarm is triggered.

In some examples, the upper and lower alarm limits are automatically set by the alarm application 126 based on demographic data of the patient P, including the age and gender of the patient P, by acquiring the demographic data from the electronic medical record 302 in the EMR system 300 via the communications network 110. Alternatively, the clinician can manually set the upper and lower alarm limits based on the demographic data of the patient P.

In some examples, the upper and lower alarm limits in the normal alarm mode 140 are set by the alarm application 126 or the clinician according to personalized baselines of the patient P. For example, when the patient P is known to have a pre-existing condition that causes low blood pressure, the lower alarm limit for blood pressure can be set lower than 90/60 mmHg. Similarly, when the patient P is known to have a pre-existing condition that causes high blood pressure, the upper alarm limit for blood pressure can be set higher than 140/90 mmHg.

In certain scenarios, it may be desirable to monitor physiological data of the patient P based on the patient P's progress during treatment. As an illustrative example, sepsis can cause the patient P to have low blood pressure. In response to a sepsis diagnosis, a clinician can intervene by administering a vasopressor medication to raise the blood pressure of the patient P. The clinician will then closely monitor the patient P to make sure that their blood pressure is increasing. As long as the blood pressure of the patient P is increasing, there is no cause for alarm. However, in such a scenario, fixed upper and lower alarm limits can lead to alarm fatigue because the lower alarm limit will be continuously triggered until the patient P's blood pressure stabilizes. In some instances, the clinician may decide to turn off the alarm which is undesirable. Alternatively, the clinician can manually reset the lower alarm limit as the condition of the patient P improves, however, this is labor-intensive and can lead to clinician burnout. Thus, fixed upper and lower alarm limits may be undesirable in such a scenario.

The crisis alarm mode 142 self-adjusts an upper or lower alarm limit in a targeted direction 144 until exit criteria 150 are met. A clinician can select the crisis alarm mode 142 when the patient P is receiving treatment that causes the data from the physiological sensor 108 to change in the targeted direction 144. When the exit criteria 150 are met, the crisis alarm mode 142 ends and the alarm application 126 returns to the normal alarm mode 140.

As shown in FIG. 4, the targeted direction 144 can include an increasing targeted direction 146 or a decreasing targeted direction 148. As an illustrative example, the increasing targeted direction 146 is selected when vasopressor medication is administered to raise the blood pressure of the patient P. As another illustrative example, the decreasing targeted direction 148 is selected when a medication or treatment is provided to decrease the heart rate of the patient P.

An alarm is triggered in the crisis alarm mode 142 when the physiological data values from the physiological sensor 108 move in a direction opposite of the targeted direction 144. For example, an alarm is triggered when the increasing targeted direction 146 is selected and the physiological data values are decreasing. As another example, an alarm is triggered when the decreasing targeted direction 148 is selected and the physiological data values are increasing.

Additional types of targeted direction may also include recovery trend lines, curves, and the like. In such examples, an alarm is triggered in the crisis alarm mode 142 when a predetermined distance from the selected recovery trend line or curve is detected.

The targeted direction 144 can be automatically selected by the alarm application 126, such as by using an algorithm that determines the targeted direction 144 based on the status or condition of the patient P (e.g., patient P is septic), and the medications and/or treatment provided to the patient P (e.g., (vasopressor medication administered to patient P). This information can be acquired by the alarm application 126 from the electronic medical record 302 of the patient P in the EMR system 300 via the communications network 110.

Alternatively, the targeted direction 144 can be selected by the clinician. For example, in embodiments where the display device 114 is a touchscreen, the clinician can select the targeted direction 144 using the display device 114. Alternatively, the clinician can select one or more user input buttons on the monitor device 104 to select the targeted direction 144.

The exit criteria 150 can include a target value 152 and a time limit 154. In some examples, only the target value 152 is selected for determining when the crisis alarm mode 142 ends. In alternative examples, both the target value 152 and the time limit 154 are selected.

The target value 152 is a physiological measurement that is within a normal range, such as one based on the demographics of the patient P (e.g., a blood pressure between 140/90 mmHg and 90/60 mmHg for adult humans). When the target value 152 is reached, the crisis alarm mode 142 ends, and the alarm application 126 returns to the normal alarm mode 140.

The time limit 154 is a predetermined time that is set based on the condition, medications, or treatment of the patient P. For example, the time limit 154 can be set for 1 hour after a medication has been administered. In some examples, the crisis alarm mode 142 ends when the target value 152 is satisfied or the time limit 154 is satisfied, whichever occurs first. Alternatively, the crisis alarm mode 142 ends when both the target value 152 and the time limit 154 are satisfied. In some examples, the exit criteria 150 are selected such that the target value 152 must be reached within the time limit 154, in order for the crisis alarm mode 142 to end.

The exit criteria 150 can be automatically set by the alarm application 126 based on the demographic data, health status, diagnoses, medications, and/or treatments administered to the patient P. The alarm application 126 can acquire this information from the electronic medical record 302 of the patient P through access to the EMR system 300 via the communications network 110. Alternatively, the exit criteria 150 can be manually set by the clinician using the display device 114 or one or more user input buttons on the monitor device 104.

As shown in FIG. 4, the crisis alarm mode 142 further includes a sensitivity level 156 that is adjustable for the self-adjustment of an upper or lower alarm limit in the targeted direction 144. For example, the sensitivity level 156 can be selected between high, medium, and low levels of sensitivity. The sensitivity level 156 can be automatically set by the alarm application 126 based on the demographic data, health status, diagnoses, medications, and/or treatments of the patient P. Alternatively, the sensitivity level 156 can be manually set by the clinician using the display device 114 or one or more user input buttons on the monitor device 104.

Figure 5:
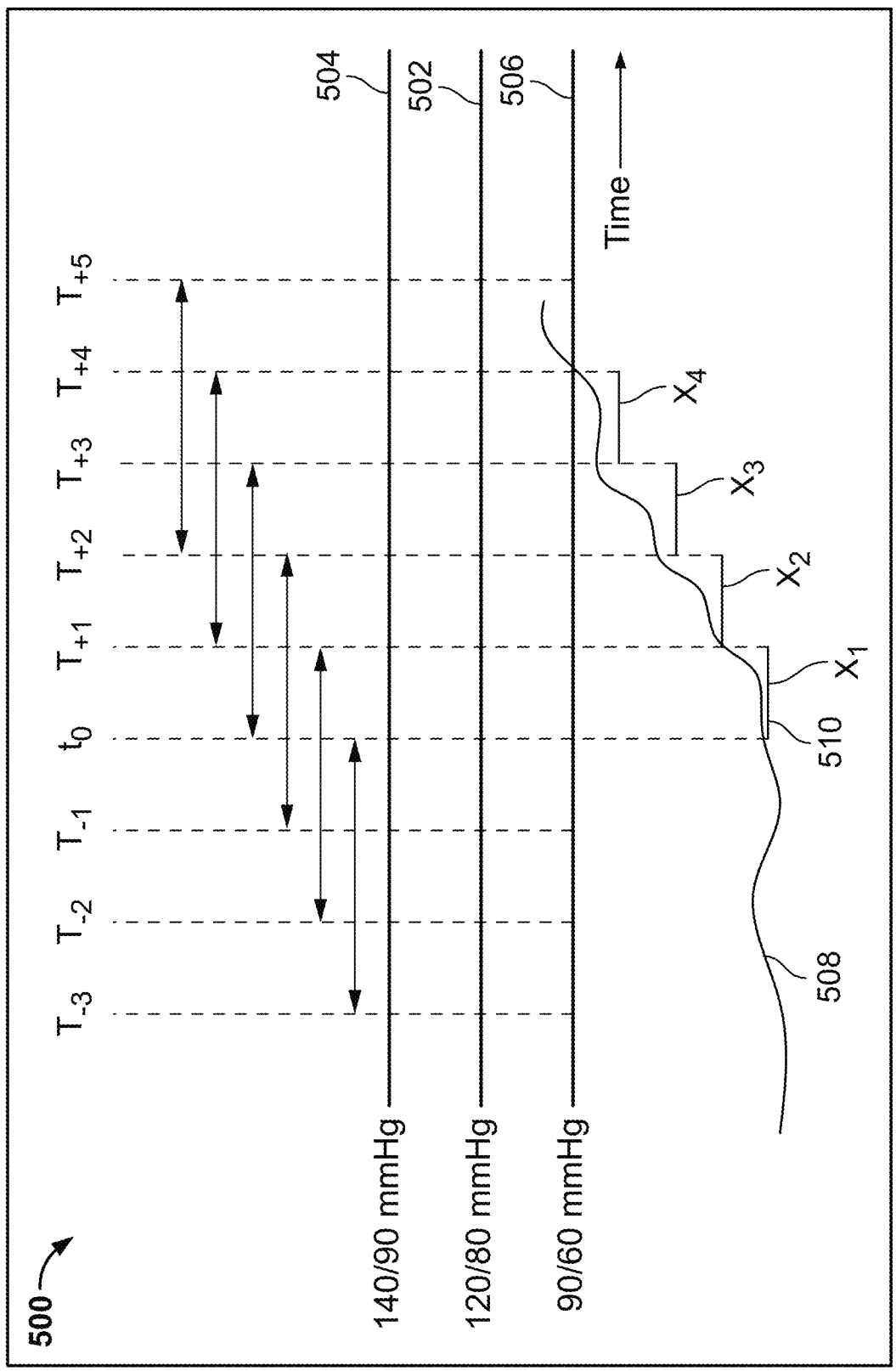
FIG. 5 illustrates an example of a crisis alarm mode in the alarm application of FIG. 4 applied to a chart displayed on the monitor device of FIG. 3.

FIG. 5 illustrates an example of the crisis alarm mode 142 applied to a chart 500 for monitoring a vital sign. In the example shown in FIG. 5, the monitored vital sign is blood pressure, and the chart 500 includes a normal resting value 502 set at 120/80 mmHg, an upper alarm limit 504 set at 140/90 mmHg, and a lower alarm limit 506 set at 90/60 mmHg. The blood pressure of the patient is represented by trend line 508. In this example, the patient is experiencing an abnormally low blood pressure (e.g., due to sepsis), and a treatment is administered to the patient (e.g., vasopressor medication) at a time of treatment $T_0$ to raise their blood pressure to a target value between the upper and lower alarm limits 504, 506.

As shown in FIG. 5, a self-adjusting lower alarm limit 510 is initially set at a starting value $X_1$ based on an abnormal state of the blood pressure before the time of treatment $T_0$. In this example, the starting value $X_1$ is based on blood pressure measurements collected during a sliding window defined as a time interval between $T_{-3}$ and $T_0$. The self-adjusting lower alarm limit 510 is set at time $T_0$ to be lower than the lower alarm limit 506 of 90/60 mmHg.

In one embodiment, a percentile is calculated from the physiological data values (e.g., blood pressure) acquired from the physiological sensor 108 during a first sliding window between time $T_{-3}$ and $T_0$, and the self-adjusting lower alarm limit 510 is initially set to the calculated percentile starting at the time of treatment $T_0$. A percentile is a physiological data value below which a given percentage of physiological data values within the first sliding window falls (exclusive definition), or at or below which a given percentage of physiological data values within the first sliding window falls (inclusive definition). The percentile can be set at any given percentage such as a 99th percentile, a 95th percentile, and the like.

In another embodiment, an average is calculated from the physiological data values (e.g., blood pressure) acquired from the physiological sensor 108 during the first sliding window between time $T_{-3}$ and $T_0$, and the self-adjusting lower alarm limit 510 is initially set a standard deviation away from the average of the physiological data values at the time of treatment $T_0$. A standard deviation is a measure of the amount of variation or dispersion of the physiological data values during the first sliding window. Additional algorithms for determining the starting value and subsequent self-adjustments of the self-adjusting lower alarm limit 510 are contemplated.

The blood pressure is monitored during a continuum of sliding windows until one or more of the exit criteria 150 are satisfied. During each sliding window, physiological data values are acquired from the physiological sensor 108, and at the end of the sliding window, an adjustment of the self-adjusting lower alarm limit 510 is determined.

As shown in the example provided in FIG. 5, a second sliding window between time $T_{-2}$ and $T_{+1}$ triggers an automatic adjustment of the self-adjusting lower alarm limit 510 from the starting value $X_1$ to a new value $X_2$. Similarly, a third sliding window between time $T_{-1}$ and $T_{+2}$ triggers an automatic adjustment of the self-adjusting lower alarm limit 510 from the previous value $X_2$ to a new value $X_3$, a fourth sliding window between time $T_0$ and $T_{+3}$ triggers an automatic adjustment of the self-adjusting lower alarm limit 510 from the previous value $X_3$ to a new value $X_4$, and so on until one or more of the exit criteria 150 are satisfied.

Advantageously, the sliding windows at least partially overlap one another to provide a level of smoothing for updating the self-adjusting lower alarm limit 510. For example, the second sliding window overlaps the first sliding window between time $T_{-2}$ and $T_0$. Similarly, the third sliding window overlaps the second sliding window between time $T_{-1}$ and $T_{+1}$, the fourth sliding window overlaps the third sliding window between time $T_0$ and $T_{+2}$, and so on.

In the example shown in FIG. 5, the blood pressure is improving such that the self-adjusting lower alarm limit 510 is adjusted at the end of each sliding window in the targeted direction 144 toward the normal resting value 502. Alternatively, when the blood pressure is not improving such that the self-adjusting lower alarm limit 510 is adjusted at the end of any sliding window away from the normal resting value 502, an alarm is triggered and the alarm application 126 exits the crisis alarm mode 142 to return to the normal alarm mode 140.

The alarm triggered in the crisis alarm mode 142 can include a local alarm on the monitor device 104 such as a visual alarm (e.g., blinking red light) and/or an audible alarm (e.g., beeping noise), and/or may also include notifications sent to mobile devices carried by clinicians (e.g., smartphones), and/or notifications sent to a nurses' station. When the alarm is triggered in the crisis alarm mode 142, the alarm application 126 returns to the normal alarm mode 140.

The self-adjusting lower alarm limit 510 continues to self-adjust until either the alarm is triggered, or the exit criteria 150 are satisfied. As an illustrative example, the exit criteria 150 can include the target value 152 set at the lower alarm limit 506 (e.g., 90/60 mmHg). When the self-adjusting lower alarm limit 510 is adjusted above the lower alarm limit 506 (e.g., above 90/60 mmHg) such as at the end of a sliding window between time $T_{+1}$ and $T_{+4}$, the crisis alarm mode 142 ends and the alarm application 126 returns to the normal alarm mode 140.

In some examples, the crisis alarm mode 142 ends when the target value 152 is satisfied (e.g., 90/60 mmHg) or the time limit 154 is satisfied, whichever occurs first. Alternatively, the crisis alarm mode 142 ends only when both the target value 152 (e.g., 90/60 mmHg) and the time limit 154 are satisfied. In some further examples, the crisis alarm mode 142 ends when the target value 152 (e.g., 90/60 mmHg) is reached within the time limit 154. Additional scenarios for ending the crisis alarm mode are possible.

Each sliding window is defined by a fixed time interval. As an illustrative example, the sliding windows are defined by a time interval of 5 minutes. The size of the sliding windows can be adjusted to adjust the sensitivity level 156 of the self-adjusting lower alarm limit 510. For example, decreasing the size of the sliding windows will increase the sensitivity level 156, while increasing the size of the sliding windows will decrease the sensitivity level 156.

Additionally, adjusting the amount of overlap between the sliding windows may also be used to adjust the sensitivity level 156 of the self-adjusting lower alarm limit 510. For example, decreasing the amount of overlap will increase the sensitivity level 156, while increasing the amount of overlap will decrease the sensitivity level 156.

FIG. 5 shows the crisis alarm mode 142 applying a self-adjusting lower alarm limit that self-adjusts in an increasing targeted direction toward the lower alarm limit 506. In other examples, such as when the patient is experiencing an abnormally high blood pressure due to hypertension, the crisis alarm mode 142 can apply a self-adjusting upper alarm limit that self-adjusts in a decreasing targeted direction toward the upper alarm limit 504. In yet further examples, the crisis alarm mode 142 can apply both a self-adjusting lower alarm limit and a self-adjusting upper alarm limit that tighten or converge toward the normal resting value 502.

In alternative embodiments where a physiological variable is not continuously monitored, but is rather monitored in intervals, the crisis alarm mode 142 can trigger additional readings after an interval reading is detected as not being in the targeted direction 144. For example, when the targeted direction 144 is for blood pressure to trend down, and an interval reading is received that the blood pressure has not trended down, or the decrease in the blood pressure is too small, the crisis alarm mode 142 can trigger another reading before the next scheduled interval reading to confirm the trend. When a movement in a direction that is not the targeted direction 144 is confirmed, the alarm application 126 triggers an alarm and exits the crisis alarm mode 142. When a movement in the direction of the targeted direction 144 is confirmed, the alarm application 126 continues to operate under the crisis alarm mode 142.

Figure 6:
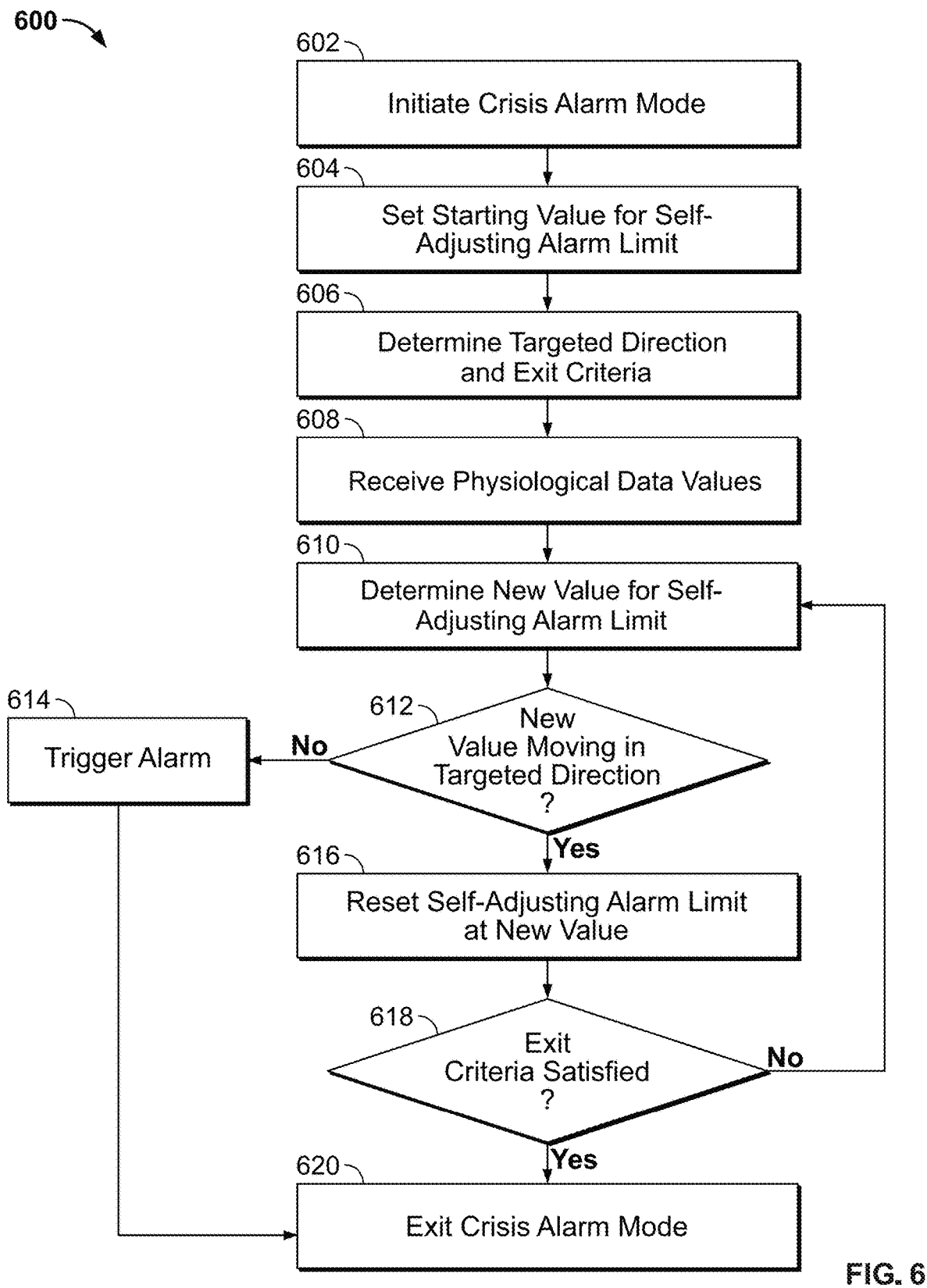
FIG. 6 illustrates an example of a method of performing the crisis alarm mode by the alarm application of FIG. 4.

FIG. 6 illustrates an example of a method 600 of performing the crisis alarm mode 142 by the alarm application 126 installed on the monitor device 104. The method 600 includes an operation 602 of initiating the crisis alarm mode 142. In some examples, the crisis alarm mode 142 is initiated upon a manual selection of the crisis alarm mode 142 from a clinician operating the monitor device 104 when the clinician intervenes to return one or more patient vital signs from an abnormal state to a normal state. In other examples, the crisis alarm mode 142 is automatically initiated by the alarm application 126 upon a determination that the clinician has intervened to return one or more patient vital signs from an abnormal state to a normal state.

Next, the method 600 includes an operation 604 of setting a starting value for a self-adjusting upper or lower alarm limit. In some examples, the starting value is the abnormal state of the vital sign captured by the physiological sensor 108 before a medical intervention.

Next, the method 600 includes an operation 606 of determining the targeted direction 144 and exit criteria 150 for the self-adjusting upper or lower alarm limit. The targeted direction 144 is determined by the alarm application 126 based on the abnormal state of the vital sign, and the normal range for the vital sign. For example, when the abnormal state is below the normal range, the targeted direction 144 is in the increasing targeted direction 146. When the abnormal state is above the normal range, the targeted direction 144 is in the decreasing targeted direction 148. The exit criteria 150 is based on the normal range for the vital sign such as an upper or lower limit for the normal range. When the upper or lower limit is reached, the alarm application 126 exits the crisis alarm mode 142 and returns to operating under the normal alarm mode 140.

Once the starting value and targeted direction for the self-adjusting upper or lower alarm limit is set, the method 600 proceeds to operation 608 of receiving a plurality of physiological data values from the physiological sensor 108 during a sliding window.

Next, the method 600 includes an operation 610 of determining a new value for the self-adjusting upper or lower alarm limit at the end of the sliding window. As described above, the new value can be based on a percentile that is calculated from the physiological data values acquired from the physiological sensor 108 during the sliding window. Alternatively, the new value can be based on a standard deviation from an average of the physiological data values.

Next, the method 600 includes an operation 612 of determining whether the new value for the self-adjusting upper or lower alarm limit is in the targeted direction 144. For example, when the abnormal state of the vital sign is low blood pressure such that the targeted direction 144 is increasing toward a normal resting blood pressure value, operation 612 determines whether a new value for a self-adjusting lower alarm limit has increased. Alternatively, when the abnormal state of the vital sign is high blood pressure such that the targeted direction 144 is decreasing toward a normal resting blood pressure value, operation 612 determines whether a new value for a self-adjusting upper alarm limit has decreased.

When the new value for the self-adjusting upper or lower alarm limit is not in the targeted direction 144 (i.e., "No" at operation 612), the method 600 proceeds to an operation 614 of triggering an alarm because the abnormal state of the vital sign is not improving, but is rather deteriorating. After the alarm is triggered, the alarm application 126 exits the crisis alarm mode 142 at operation 620 where it returns to operating under the normal alarm mode 140 where the upper and lower alarm limits for monitoring the vital sign are fixed values.

When the new value for the self-adjusting upper or lower alarm limit is in the targeted direction 144 (i.e., "Yes" at operation 612), the method 600 proceeds to operation 616, which includes resetting the self-adjusting upper or lower alarm limit to the new value. As discussed above, the new value for the self-adjusting upper or lower alarm limit can be based on a percentile that is calculated from the physiological data values acquired from the physiological sensor 108 during the sliding window. Alternatively, the new value can be based on a standard deviation from an average of the physiological data values during the sliding window.

The method 600 includes an operation 618 of determining whether the exit criteria 150 are satisfied. The exit criteria 150 can include a target value 152 and/or a time limit 154. When the exit criteria 150 are satisfied (i.e., "Yes" at operation 618), the alarm application 126 exits the crisis alarm mode 142 at operation 620. When the exit criteria 150 are not satisfied (i.e., "No" at operation 618), the alarm application 126 repeats the operations 610-618.

Figure 7:
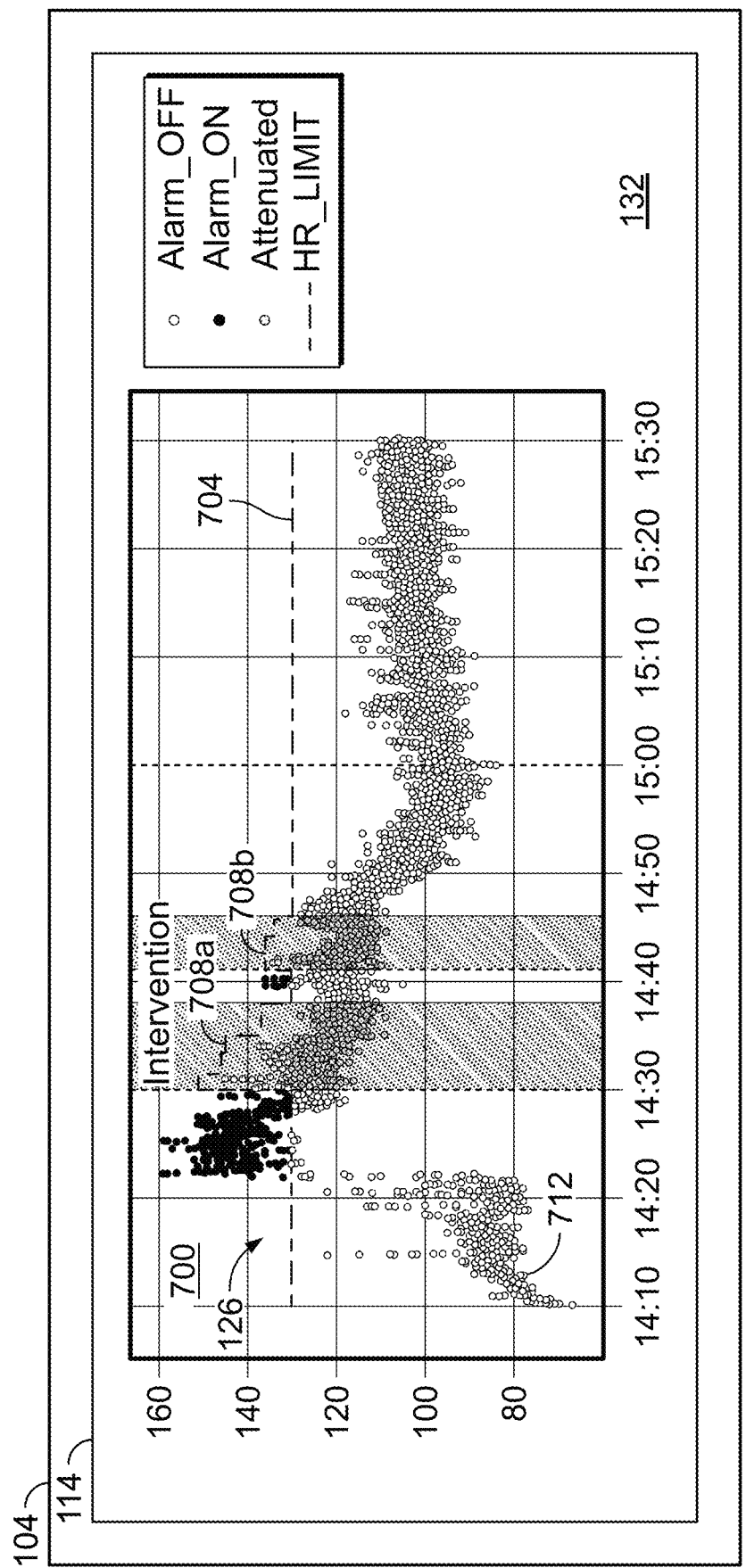
FIG. 7 illustrates an example of the alarm application of FIG. 4 applied to a chart displayed on the monitor device of FIG. 3.

FIG. 7 illustrates an example of the alarm application 126 applied to a chart 700 for monitoring a vital sign. The chart 700 is displayed on the display device 114 of the monitor device 104. In FIG. 7, the monitored vital sign is heart rate, and the chart 700 includes an upper alarm limit 704 set at 130 beats per minute (BPM). The upper alarm limit 704 can be a default upper alarm limit, or can be based on the patient's stable baseline before the onset of a health crisis that causes the patient's heart rate to reach an abnormal state.

In some examples, the patient's stable baseline is captured while the vital sign (e.g., heart rate) was stationary at any time before it changed to the abnormal state. In certain examples, an Augmented Dickey-Fuller (ADF) test is performed to test for stationarity at admission (and periodically afterwards) to determine the patient's stable baseline. In some examples, a clinician decides whether to accept or reject the captured stable baseline.

In FIG. 7, the heart rate is monitored under the normal alarm mode 140 before an intervention by a clinician occurs at 14:30. While under the normal alarm mode 140, physiological data values 712 (e.g., heart rate measurements acquired from the physiological sensor 108) experience a sudden increase after 14:20 and begin to exceed the upper alarm limit 704 such that the alarm is triggered under the normal alarm mode 140.

After the intervention by the clinician at 14:30, the heart rate is monitored under the crisis alarm mode 142 which establishes a self-adjusting upper alarm limit 708*a* based on the abnormally high heart rate measured at the time of the intervention. The self-adjusting upper alarm limit 708a is higher than the upper alarm limit 704 set at 130 BPM.

The self-adjusting upper alarm limit 708a continuously decreases in the targeted direction 144 until it reaches the upper alarm limit 704, at which point the alarm application 126 exits the crisis alarm mode 142 and continues to monitor the heart rate under the normal alarm mode 140. In this example, the alarm application 126 exits the crisis alarm mode 142 because the target value 152 (e.g., 130 BPM) of the exit criteria 150 is satisfied. While under the crisis alarm mode 142, the alarm is suppressed, thereby reducing alarm fatigue.

In the example of FIG. 7, there is a second health crisis at about 14:40 that causes the patient's heart rate to increase beyond the upper alarm limit 704 while the heart rate is being monitored under the normal alarm mode 140. The clinician intervenes such that the heart rate is monitored under the crisis alarm mode 142 for a second time which establishes a self-adjusting upper alarm limit 708b based on the abnormally high heart rate measured at the time of the second intervention. While under the crisis alarm mode 142, the alarm is suppressed, thereby reducing alarm fatigue. The self-adjusting upper alarm limit 708b decreases in the targeted direction 144 until it reaches the upper alarm limit 704, at which point the alarm application 126 exits the crisis alarm mode 142 because the target value 152 is reached, and the alarm application 126 monitors the heart rate under the normal alarm mode 140.

Figure 8:
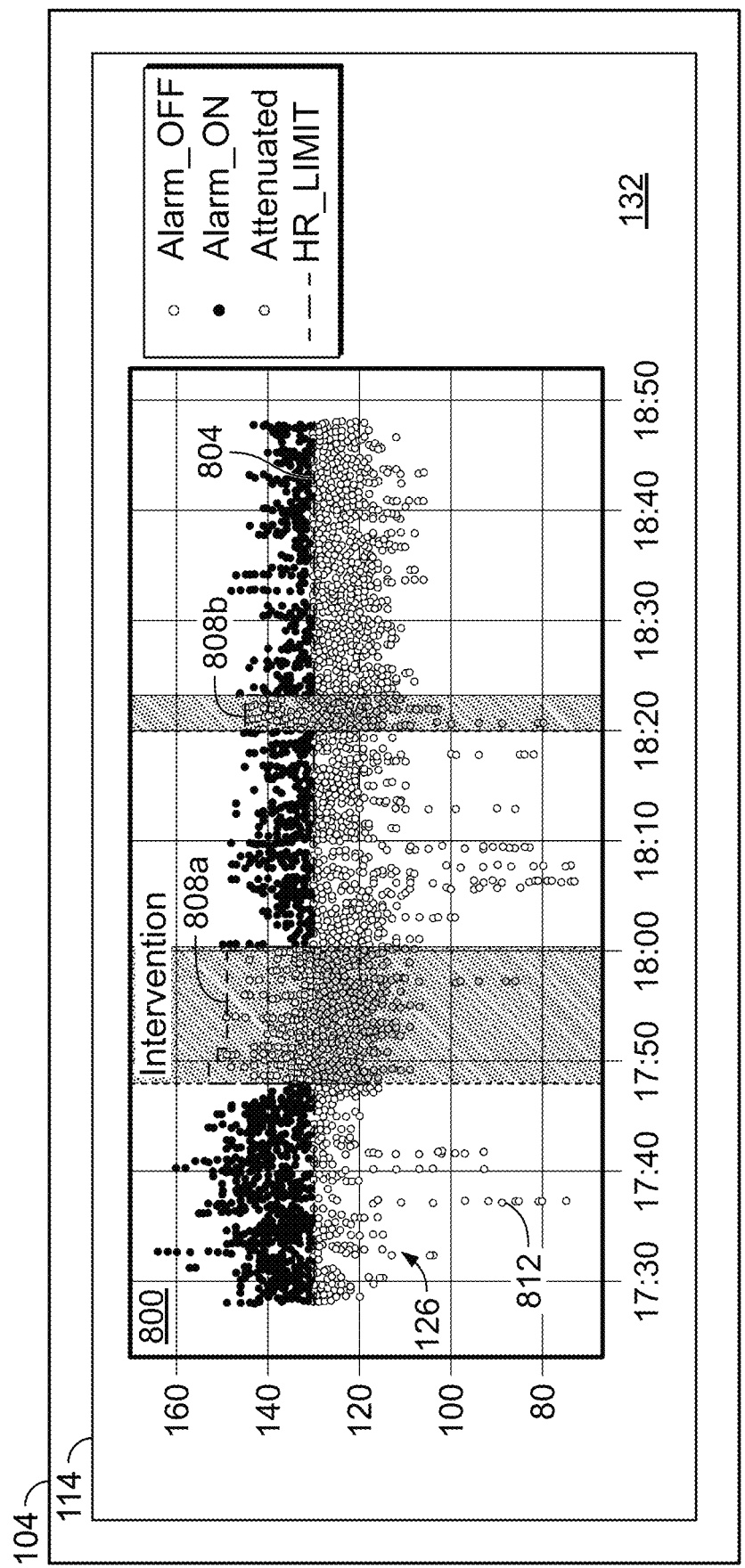
FIG. 8 illustrates another example of the alarm application of FIG. 4 applied to a chart displayed on the monitor device of FIG. 3.

FIG. 8 illustrates another example of the alarm application 126 applied to a chart 800 for monitoring a vital sign. As shown in FIG. 8, the chart 800 is displayed on the display device 114 of the monitor device 104. Like in the examples described above, the monitored vital sign is heart rate, and the chart 800 includes an upper alarm limit 804 set at 130 BPM. In this example, the heart rate is monitored under the normal alarm mode 140 until an intervention by a clinician occurs at about 17:50. After the intervention by the clinician, the heart rate is monitored under the crisis alarm mode 142 which establishes a self-adjusting upper alarm limit 808a based on the abnormally high heart rate measured at the time of the intervention.

The self-adjusting upper alarm limit 808a is higher than the upper alarm limit 804 set at 130 BPM. The self-adjusting upper alarm limit 808a decreases in the targeted direction 144 until about 18:00, at which point the physiological data values 812 acquired from the physiological sensor 108 exceed the self-adjusting upper alarm limit 808a. The alarm is triggered and the alarm application 126 exits the crisis alarm mode 142 to return to the normal alarm mode 140. In this example, the target value 152 (e.g., 130 BPM) is not reached and the self-adjusting upper alarm limit 808a increased away from the targeted direction 144. Advantageously, the crisis alarm mode 142 in this example notifies the clinician that the patient did not respond to the intervention as expected, such that an additional intervention is needed.

In the example of FIG. 8, there is a second intervention at about 18:20 such that the heart rate is monitored under the crisis alarm mode 142 for a second time which establishes a self-adjusting upper alarm limit 808b based on the abnormally high heart rate measured at the time of the second intervention. The self-adjusting upper alarm limit 808b decreases in the targeted direction 144 until the physiological data values 812 exceed the self-adjusting upper alarm limit 808b, at which point the alarm is triggered and the alarm application 126 exits the crisis alarm mode 142 to return to monitoring heart rate under the normal alarm mode 140.

Figure 9:
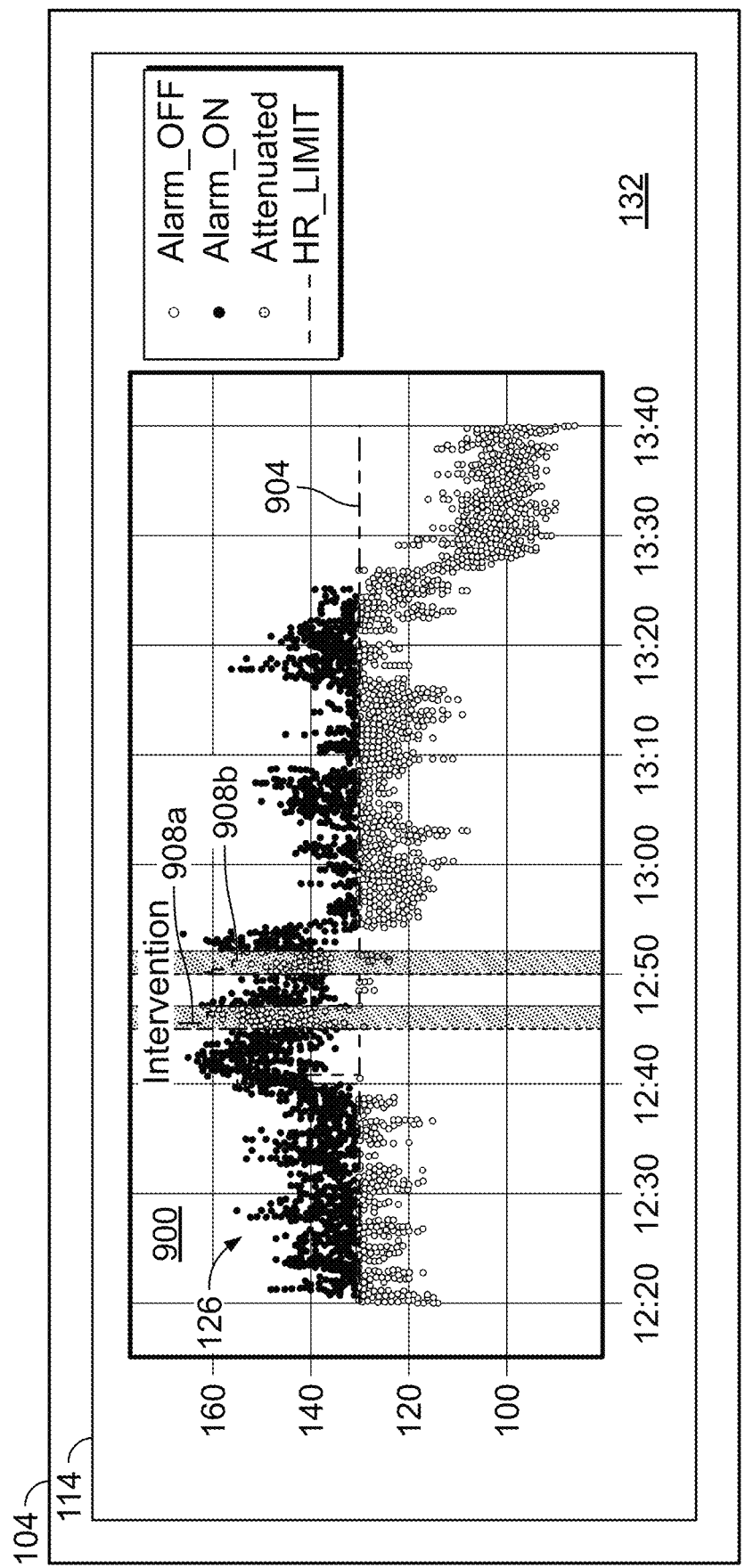
FIG. 9 illustrates another example of the alarm application of FIG. 4 applied to a chart displayed on the monitor device of FIG. 3.
Figure 10:
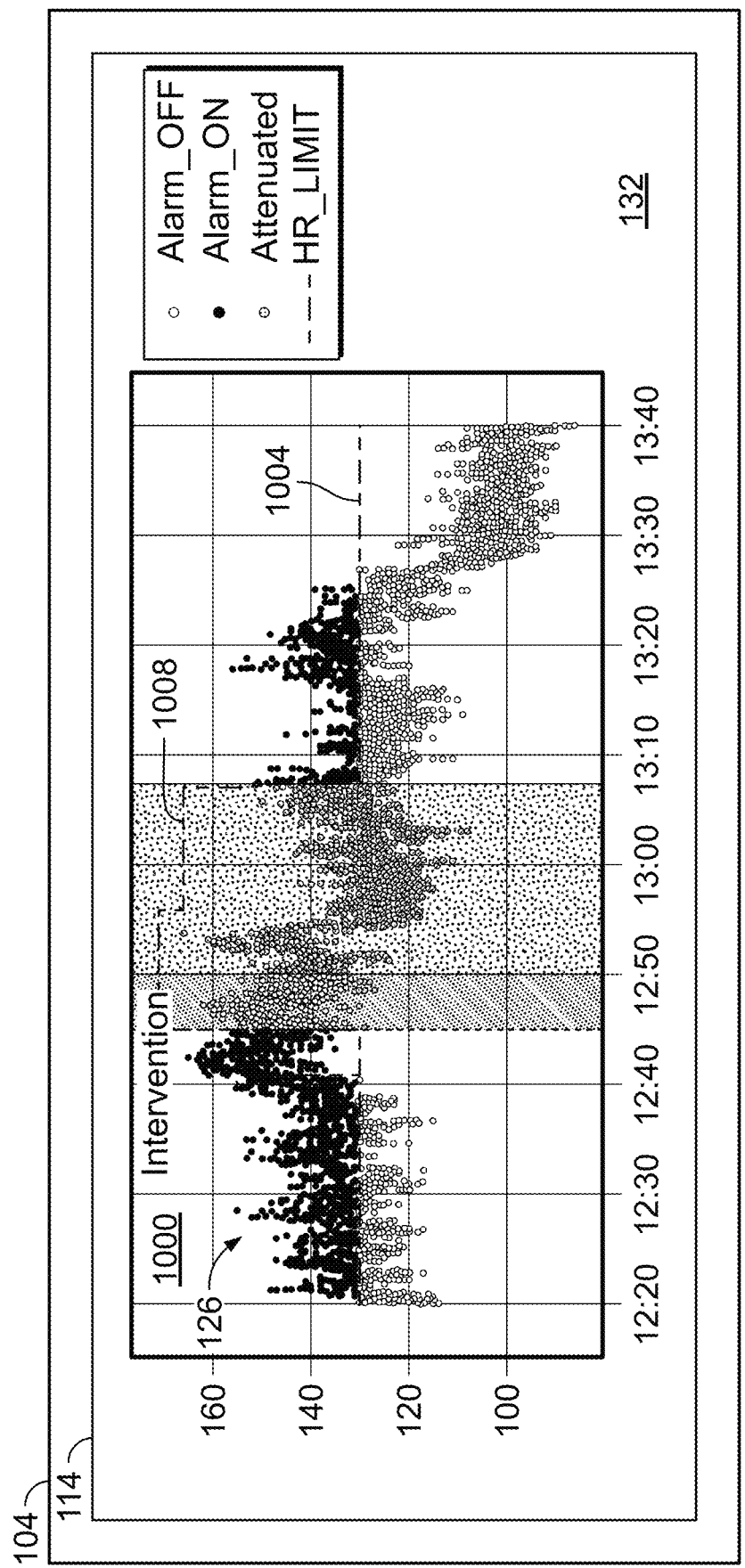
FIG. 10 illustrates another example of the alarm application of FIG. 4 applied to a chart displayed on the monitor device of FIG. 3.

FIGS. 9 and 10 illustrate examples of the alarm application 126 applied to charts 900, 1000 having the same physiological data values for monitoring a vital sign such as heart rate. FIGS. 9 and 10 illustrate an example where the size of the sliding window (see FIG. 5) is adjusted, to control the sensitivity level 156 of the crisis alarm mode 142.

In FIG. 9, the sliding window is smaller such that the sensitivity level 156 of the crisis alarm mode 142 is more sensitive. In FIG. 10, the sliding window is larger such that the sensitivity level 156 of the crisis alarm mode 142 is less sensitive.

In FIG. 9, there is a first intervention at about 12:45 such that the heart rate is monitored under the crisis alarm mode 142 which establishes a self-adjusting upper alarm limit 908a based on the abnormally high heart rate measured at the time of the first intervention. The self-adjusting upper alarm limit 908a is higher than the upper alarm limit 904 set at 130 BPM. The self-adjusting upper alarm limit 908a begins to decrease in the targeted direction 144, until the physiological data values acquired from the physiological sensor 108 exceed the self-adjusting upper alarm limit 908a such that the alarm is triggered and the alarm application 126 exits the crisis alarm mode 142 and returns to the normal alarm mode 140.

As further shown in FIG. 9, there is a second intervention at about 12:50 such that the heart rate is monitored under the crisis alarm mode 142 which establishes a self-adjusting upper alarm limit 908b based on the abnormally high heart rate measured at the time of the second intervention. The self-adjusting upper alarm limit 908b is higher than the upper alarm limit 904, and decreases in the targeted direction 144 until the physiological data values exceed the self-adjusting upper alarm limit 908b such that the alarm is triggered again and the alarm application 126 exits the crisis alarm mode 142 and returns to the normal alarm mode 140.

In FIG. 10, the sliding window is larger such that the sensitivity level 156 of the crisis alarm mode 142 is less sensitive. Thus, after the intervention at about 12:45, the crisis alarm mode 142 establishes a self-adjusting upper alarm limit 1008a which decrease in the targeted direction 144 until it reaches the upper alarm limit 1004, such that the target value 152 is satisfied. At this point, the alarm application 126 exits the crisis alarm mode 142 and returns to the normal alarm mode 140 for monitoring the physiological data values. Thus, unlike in FIG. 9, the alarm in FIG. 10 is not triggered during the crisis alarm mode 142 due to the lower level of sensitivity that results from having a larger sliding window.

Figure 11:
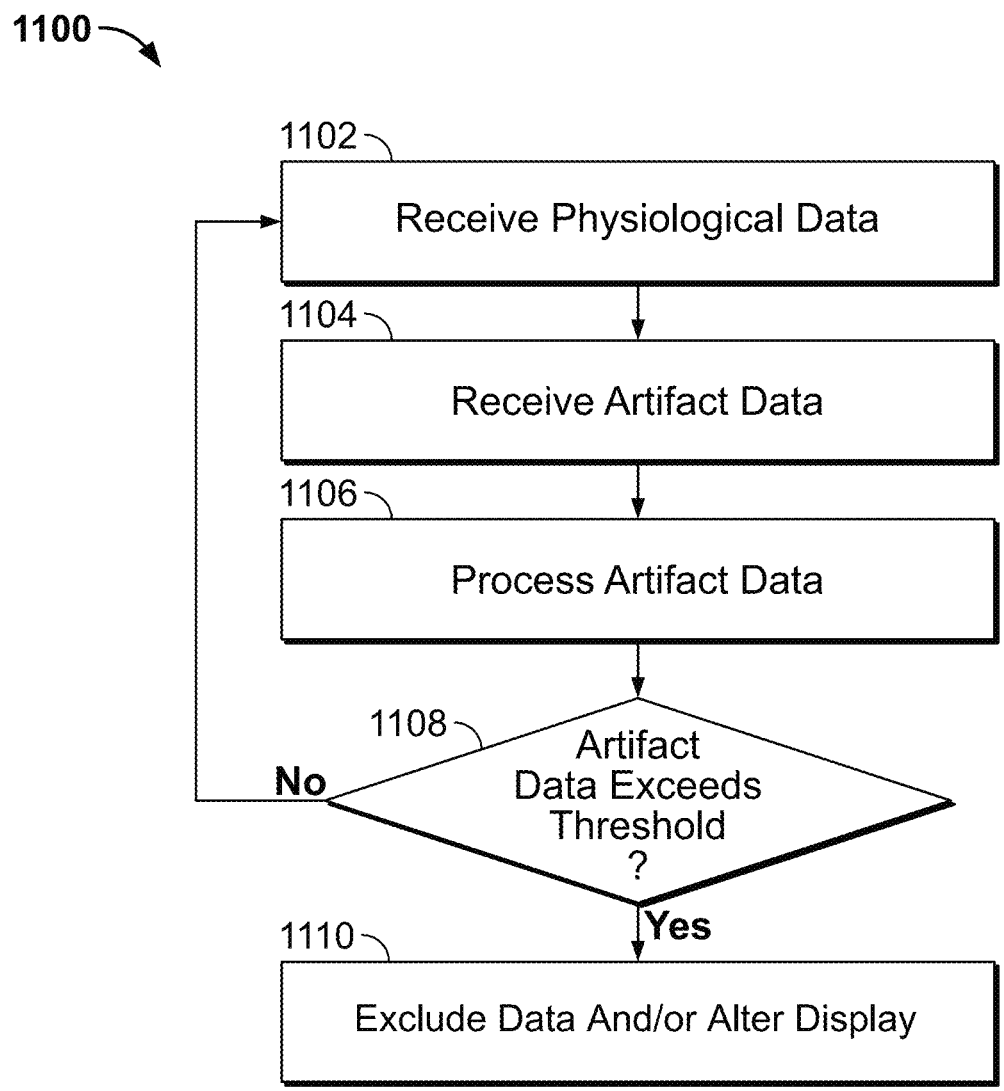
FIG. 11 illustrates an example of a method of continuous physiological monitoring performed by a visualization application installed on the monitor device of FIG. 3.

FIG. 11 illustrates an example of a method 1100 of continuous physiological monitoring performed by the visualization application 128 installed on the monitor device 104. The method 1100 is performed to provide additional context and information regarding physiological data captured from the physiological sensor 108 to boost confidence in the data and aid decision making by a clinician. The method 1100 can be performed to improve the fidelity of the self-adjusting alarm limits, and/or to alter the display of the physiological data on the display device 114, which can help the clinician to decide whether to adjust an alarm setting, determine whether a medical intervention is needed, or initiate the crisis alarm mode 142.

The alarm application 126 and visualization application 128 can operate together on the monitor device 104 such that the method 1100 can be performed in combination or in parallel with the method 600. For example, the monitor device 104 can operate under both the normal and crisis alarm modes while altering the display of the physiological data on the display device 114 to provide additional context and information regarding the physiological data to help aid decision making by a clinician such as whether to initiate or exit the crisis alarm mode 142.

The method 1100 includes an operation 1102 of receiving physiological data from the physiological sensor 108. The physiological data can include heart rate, respiration rate, blood pressure, blood oxygen saturation (SpO2), end tidal carbon dioxide (etCO2), and the like.

The method 1100 includes an operation 1104 of receiving artifact data that may affect or influence the physiological data received from the physiological sensor 108. For example, the artifact data may cause the physiological data to be inaccurate, erroneous, and/or false. The artifact data can be received simultaneously as the physiological data. In some instances, the artifact data is time stamped and the physiological data is time stamped, and the time stamps of the artifact data and the physiological data are matched together for correspondence.

The artifact data can include audio sounds captured from the audio sensor 116. As described above, the audio sounds captured from the audio sensor 116 can be used to detect when the patient P is coughing, talking, and eating, which can affect or influence physiological data such as the respiration rate and etCO2 data sensed by the physiological sensor 108. Additionally, artifact data can include motion data detected by the motion sensor 106 such as movements by the patient P while being supported on the patient support system 102, and/or a video feed captured by a camera that detects movements by the patient P inside the area 10. Additional sources of artifact data that can be received in operation 1104 are contemplated.

Alternatively, or in addition to the audio sounds, the artifact data can include motion data captured by the motion sensor 106, which can affect or influence physiological data such as the heart rate, blood pressure, or respirate rate data sensed by the physiological sensor 108. As described above, the motion data can be captured from piezoelectric sensors, load cells, or combinations thereof that are positioned below, within, or on top of a mattress 112 of the patient support system 102, from one or more accelerometers attached to the patient P, or from an accelerometer incorporated into the physiological sensor 108, which is attached to the patient P.

Next, the method 1100 includes an operation 1106 of processing the artifact data. In some examples, the artifact data is processed to classy the artifact data as either coughing, talking, or eating, which can affect or influence the respiration rate and etCO2 data, or as motion data that can affect or influence the heart rate, blood pressure, or respirate rate data. Additionally, the artifact data can be processed to quantify and/or classify a strength of the detected artifact data, such as corresponding to an amount of coughing, talking, and eating (e.g., talking vs. shouting), or an amount or type of motion (rolling to one side of the patient support system 102 vs. getting up and leaving the patient support system 102 to walk around the area 10).

The method 1100 includes an operation 1108 of determining whether the artifact data exceeds a predetermined threshold amount, such that the artifact data is strong enough to influence the physiological data. When the artifact data is less than the predetermined threshold amount (i.e., "No" at operation 1108), the method 1100 continues to monitor the physiological data by repeating the operations 1102-1108. When the artifact data exceeds the predetermined threshold amount (i.e., "Yes" at operation 1108), the method 1100 proceeds to operation 1110, which can include excluding artifact affected physiological data from consideration when adjusting the one or more self-adjusting alarm limits (see the method 600). Additionally, or alternatively, operation 1110 can include altering the display of the physiological data on the display device 114, which will now be described with reference to FIGS. 12 and 13.

Figure 12:
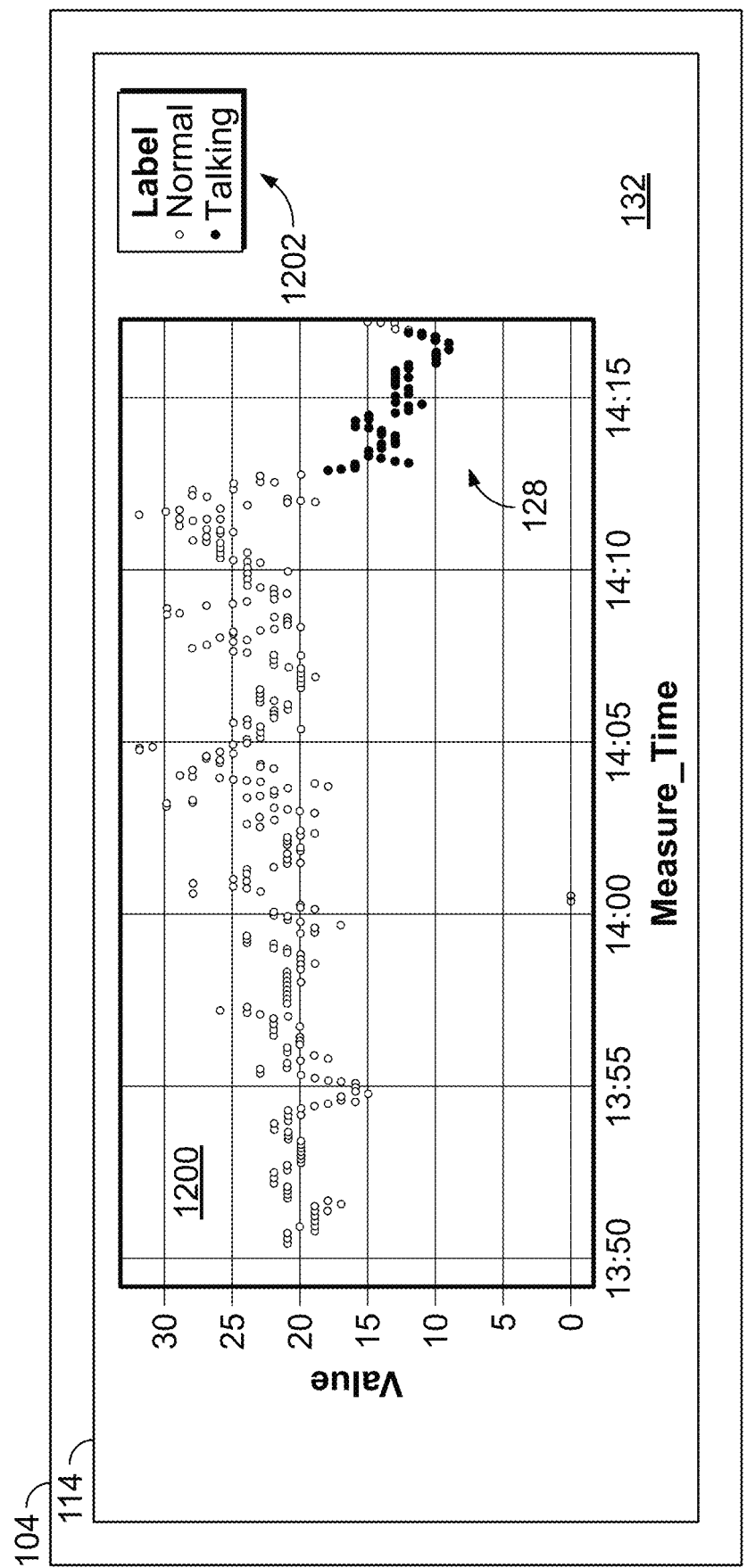
FIG. 12 illustrates an example of the visualization application applied to a chart displayed on the monitor device of FIG. 3.

FIG. 12 illustrates an example of the visualization application 128 applied to a chart 1200 displayed on the display device 114 of the monitor device 104, in accordance with operation 1110 of the method 1100. In the example shown in FIG. 12, the chart 1200 is for monitoring respiration rate values. The visualization application 128 displays the respiration rate values differently based on when the patient P is detected as talking (e.g., when the artifact data exceeds a predetermined threshold amount) or when the patient P is not talking (e.g., when the artifact data does not exceed the predetermined threshold amount). While the chart 1200 displays respiration rate values, the visualization application 128 can be applied in a similar fashion to charts that display other types of physiological data values such as heart rate, blood pressure, blood oxygen saturation (SpO2), end tidal carbon dioxide (etCO2), and the like.

In FIG. 12, the respiration rate values when the patient P is talking are displayed in a color (e.g., red) that is different from a color (e.g., blue) of the respiration rate values when the patient P is not talking such that the respiration rate values are color coded. In other examples, the visualization application 128 can apply a different kind of dashed line pattern or other type of visual marker to distinguish between the respiration rate values detected when the patient P is talking from the respiration rate values detected when the patient P is not talking.

In FIG. 12, the chart 1200 includes a legend 1202 that includes labels identifying visual markers associated with artifacts that can affect or influence the respiration rate values, such as when the patient P is talking (e.g., "Talking"). The visual markers can also be associated with normal behavior (e.g., "Normal") when no artifacts are detected.

The legend can include additional labels for visual markers associated with coughing and eating artifacts when the audio sensor 116 detects that the patient P is coughing or eating, and for additional visual markers associated with motion when the motion sensor 106 detects the patient P is moving. In some examples, the legend 1202 classifies the artifacts detected by the audio sensor 116 and motion sensor 106 together under one label such as "Artifact detected", without distinguishing between talking, coughing, eating, and motion artifacts.

As described above, the alarm application 126 and visualization application 128 can operate together on the monitor device 104. Thus, the visual markers can be displayed by the visualization application 128 to classify the physiological data values when artifacts (e.g., talking, coughing, eating, and motion) are detected by the motion sensor 106 and audio sensor 116, while the monitor device 104 is operating in the normal alarm mode 140 and the crisis alarm mode 142 in accordance with the alarm application 126. Advantageously, the visual markers from the visualization application 128 can help inform a clinician to decide whether to respond to an alarm or adjust an alarm setting, determine whether a medical intervention is needed, and/or initiate the crisis alarm mode 142. Thus, the visual markers displayed by the visualization application 128 improve the operation of the monitor device 104.

Figure 13:
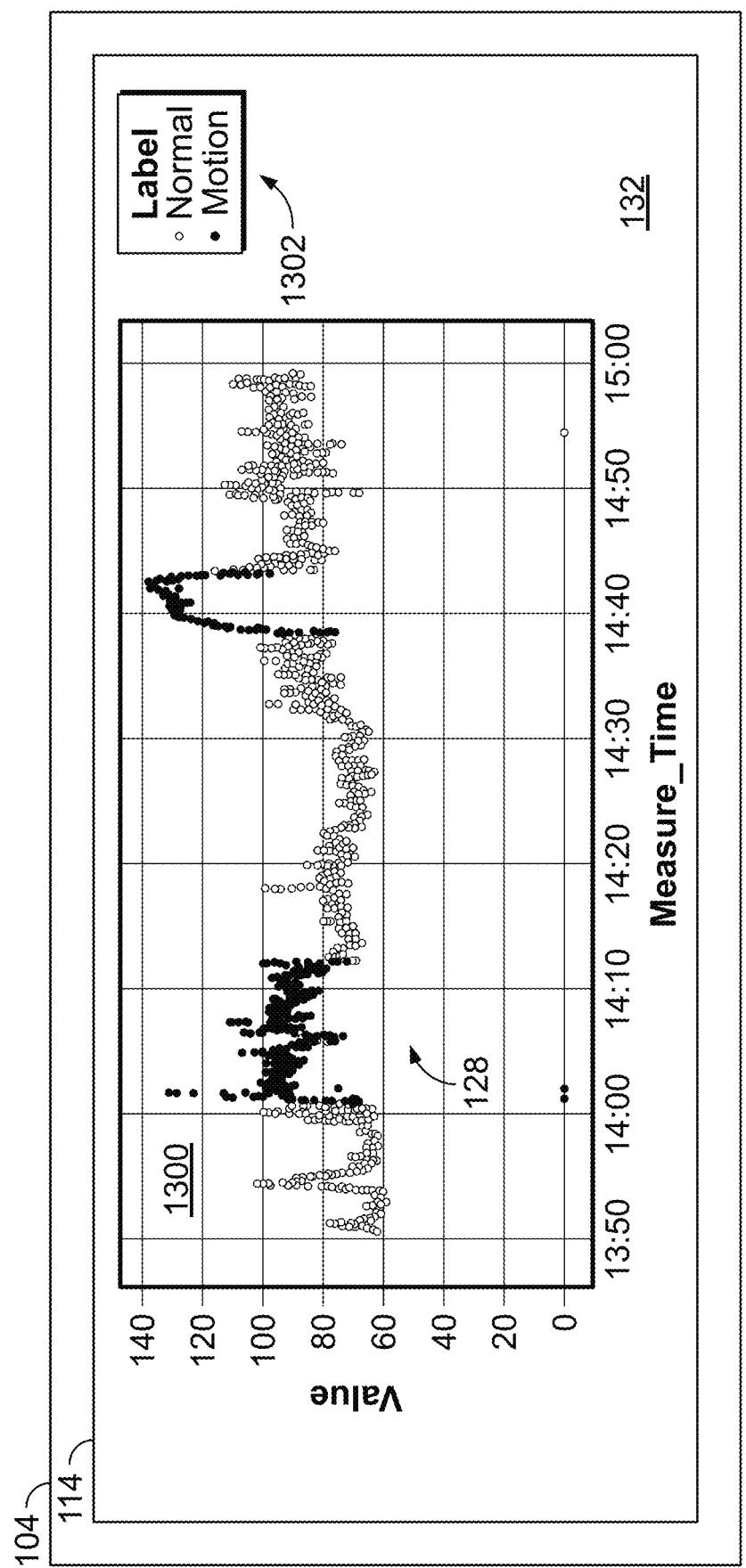
FIG. 13 illustrates another example of the visualization application applied to a chart displayed on the monitor device of FIG. 3.

FIG. 13 illustrates another example of the visualization application 128 applied to a chart 1300 displayed on the display device 114 of the monitor device 104, in accordance with operation 1110 of the method 1100. FIG. 13 is similar to the example shown in FIG. 12, except the chart 1300 is for monitoring heart rate values, which are displayed differently based on whether the patient is detected by the motion sensor 106 as moving or not moving. For example, the chart 1300 includes a legend 1302 that includes "Normal" and "Motion" labels to distinguish heart rate values when the patient is moving from when the patient is not moving.

In alternative examples to those shown in FIGS. 12 and 13, the physiological data values (e.g., heart rate, respiration rate, blood pressure, blood oxygen saturation (SpO2), end tidal carbon dioxide (etCO2), etc.) are excluded from the charts 1200, 1300 when motion artifacts (e.g., talking, coughing, eating, and motion) are detected by the motion sensor 106 and audio sensor 116. In such examples, the legends 1202, 1302 can provide explanations for the exclusion of the physiological data values, such as due to the detection of one or more artifacts. Additionally, automatic or semi-automatic baselining can be performed without using the excluded physiological data values to calculate a personalized baseline for the patient.

Figure 14:
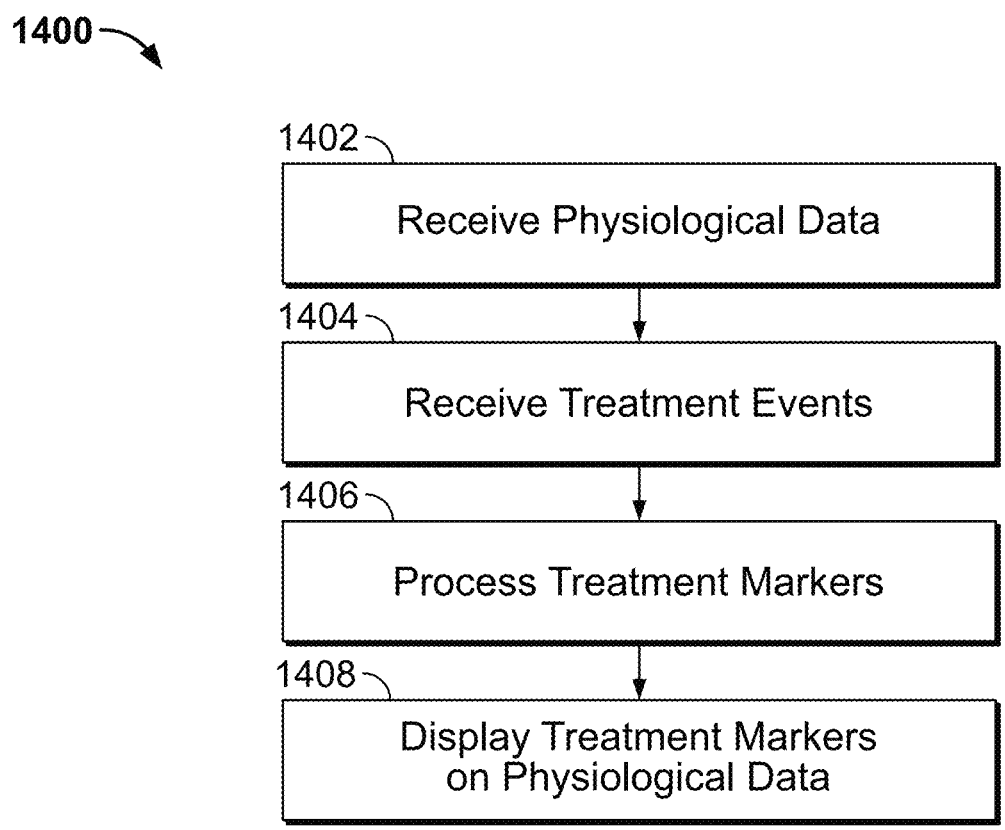
FIG. 14 illustrates another example of a method of continuous physiological monitoring performed by the visualization application installed on the monitor device of FIG. 3.

FIG. 14 illustrates another example of a method 1400 of continuous physiological monitoring performed by the visualization application 128 installed on the monitor device 104. The method 1400 is performed to provide additional context and information regarding physiological data captured from the physiological sensor 108 to boost confidence in the data and aid decision making by a clinician. The method 1400 alters the display of the physiological data on the display device 114 to help a clinician to decide whether to adjust an alarm setting, determine whether a medical intervention is needed, and/or initiate the crisis alarm mode 142.

As described above, the alarm application 126 and visualization application 128 can operate together on the monitor device 104 such that the method 1400 can be performed in combination or in parallel with the method 600. For example, the monitor device 104 can operate under both the normal and crisis alarm modes while altering the display of the physiological data on the display device 114 in accordance with the operations of the method 1400.

The method 1400 includes an operation 1402 of receiving physiological data from the physiological sensor 108. The physiological data can include heart rate, respiration rate, blood pressure, blood oxygen saturation (SpO2), end tidal carbon dioxide (etCO2), and the like.

The method 1400 includes an operation 1404 of receiving treatment events that may affect or influence the physiological data received from the physiological sensor 108. Examples of the treatment events include, without limitation, medications, surgical operations, pre-operative and post-operative procedures, diagnoses, co-morbidities, rapid response alarm codes, sepsis risk scores including systemic inflammatory response syndrome (SIRS) scores, sequential organ failure assessment scores (SOFA), and quick SOFA scores (qSOFA), Early Warning Scores (EWS), equipment requests (e.g., requests for nasal cannula, high flow, bilevel positive airway pressure (BiPap) ventilator, and the like for oxygen supply), Glasgow Modified Alcohol Withdrawal Scale (GMAWS) scores for alcohol and/or opioid withdrawal, and other treatments that may affect or influence the physiological data. The treatment events received in operation 1404 are time stamped to include information such as when they took place and for how long.

The visualization application 128 when installed on the monitor device 104 can receive the treatment events from the server 200 via the communications network 110. For example, the visualization application 128 can receive the diagnoses and co-morbidities of a patient from the electronic medical record 302 of the patient stored in the EMR system 300. As another example, the visualization application 128 can receive administered medications from the medication record 402 of the patient stored in the EMAR system 400.

Alternatively, or in addition to receiving the treatment events from the server 200, the treatment events can be entered manually into the monitor device 104 by a clinician. In examples where the display device 114 operates to display a user interface 132 that receives inputs, the clinician can manually enter the treatment events on the monitor device 104 from a drop down menu. In some instances, the drop down menu can include a treatment name or ID that the clinician can select. Alternatively, the clinician can enter the treatment name or ID into a field on the user interface 132. Also, the clinician can scan a bar code of a medication using a bar code scanner connected to the monitor device 104 to enter the medication as a treatment event.

The method 1400 includes an operation 1406 of processing the treatment events to determine whether they have an effect on one or more of the physiological variables measured by the physiological sensor 108 such as heart rate, respiration rate, blood pressure, blood oxygen saturation (SpO2), end tidal carbon dioxide (etCO2), and the like. The treatment event can be processed to determine whether it has a targeted effect (e.g., a vasopressor medication that has a targeted effect to raise blood pressure), or whether it has an unintended side effect on one or more of the physiological variables measured by the physiological sensor 108.

In some instances, the side effect can be classified as mild, medium, or severe. Additionally, the targeted effect or side effect of each treatment event can be classified or quantified as having an effect within a physiological variable range such as an absolute range or a relative range based on patient baseline values, and within a time window range.

Additionally, each treatment event is processed to determine whether it may have an interaction with any other treatment events that may cause an effect on the one or more of the physiological variables measured by the physiological sensor 108. For example, a certain medication may have a side effect based on a co-morbidity of the patient.

Next, the method 1400 includes an operation 1408 of altering the display of the physiological data on the display device 114 based on the processed treatment events. For example, all medications administered to the patient that are known to affect a physiological variable measured by the physiological sensor 108 are displayed on the display device 114 along with the measured physiological data values. Each medication can be displayed as a predefined range that is overlayed on the measured physiological data values to show a duration that the medication was administered to the patient (e.g., when administered through an IV drip), or an estimated duration that the medication may affect the measured physiological data values.

Additionally, any side effects that cause the measured physiological data values to fall within a defined range will be displayed with appropriate labels (e.g., listing possible causes for the side effects such as due to co-morbidities, drug interactions, or other causes). In some examples, the display device 114 can display one or more recommended actions such as to adjust alarm settings, adjust medications, check patient response, or provide a medical intervention.

Figure 15:
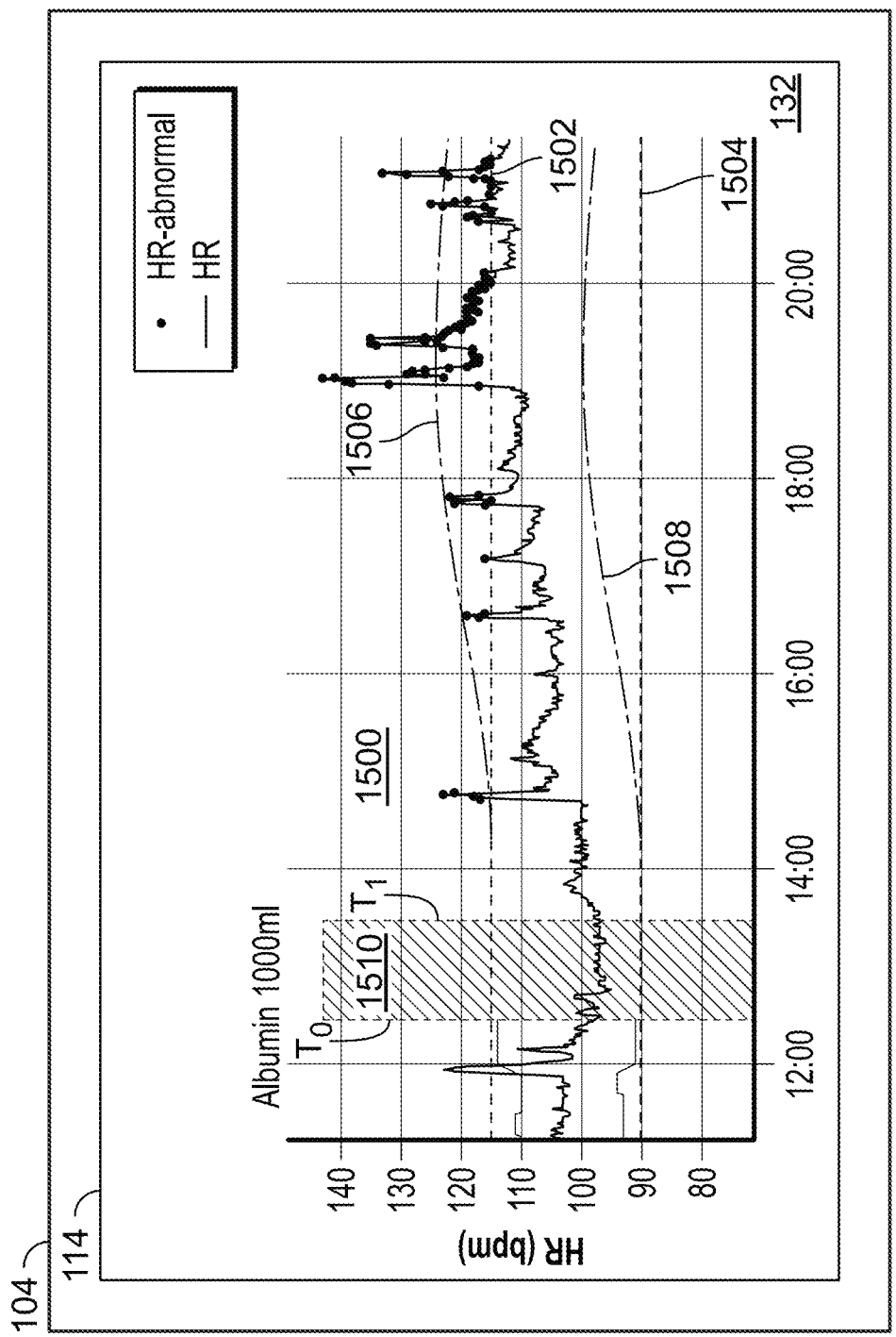
FIG. 15 illustrates another example of the visualization application applied to a chart displayed on the monitor device of FIG. 3.

FIG. 15 illustrates another example of the visualization application 128 applied to a chart 1500 displayed on the display device 114 of the monitor device 104, in accordance with operation 1408 of the method 1100. In the example shown in FIG. 12, the chart 1500 is for monitoring heart rate values. The visualization application 128 displays the heart rate values along with one or treatment events that can affect the heart rate values. While the chart 1500 displays heart rate values, the visualization application 128 can be applied in a similar fashion to charts that display other types of physiological data values such as heart rate, blood pressure, blood oxygen saturation (SpO2), end tidal carbon dioxide (etCO2), and the like.

The chart 1500 displays a normal range for the heart rate values defined by upper and lower limits 1502, 1504. In some examples, the upper and lower limits 1502, 1504 of the normal range are based on default values. Alternatively, the upper and lower limits 1502, 1504 of the normal range are based on personalized baselines of the patient. The normal range between the upper and lower limits 1502, 1504 is overlayed on the heart rate values in a first shade of color.

The chart 1500 also displays a treatment event 1510 that starts at time $T_0$ and ends at time $T_1$. In the example shown in FIG. 15, the treatment event 1510 is an albumin infusion, which is used to treat or prevent shock following serious injury, bleeding, surgery, or burns by increasing the volume of blood plasma. The treatment event 1510 between time $T_0$ and time $T_1$ is displayed as a visual marker overlayed on the heart rate values in a second shade of color.

While the example in FIG. 15 shows the chart 1500 as displaying a single treatment event, it is contemplated that the chart 1500 can display a plurality of treatment events. In such examples, a clinician can view all of the treatment events on a timeline, along with the physiological data values acquired from the physiological sensor 108.

In examples where the display device 114 operates to display a user interface 132 that receives inputs, the clinician can select the treatment event 1510 to obtain information on an expected effect or influence of the treatment event 1510 on the physiological data values acquired from the physiological sensor 108. For example, the clinician can select the treatment event 1510 with their finger or with a stylus in examples where the display device 114 is a touchscreen to obtain information on the expected effect or influence on the physiological data values acquired from the physiological sensor 108. Alternatively, or in addition, the clinician can select the treatment event 1510 using a mouse cursor or can hover the mouse cursor over the treatment event 1510 (without actually selecting the treatment event 1510) to obtain the information on the expected effect or influence on the physiological data values.

The expected effect of the treatment event 1510 can be overlaid on a trendline of the physiological data values acquired from the physiological sensor 108 that are displayed on the chart 1500. The expected effect of the treatment event 1510 can be color coded differently between ranges of desired target effect, side effect, and severe side effect that needs to be intervened immediately. This information can then be used by the clinician to adjust a treatment plan based on the expected effect, adjust alarm settings including adjusting upper and lower alarm limits to an acceptable range based on the expected effect, or intervene and set the crisis alarm mode 142. Also, some treatment events 1510 can display potential drug interactions with other medications within a configured time window to further inform the clinician.

In FIG. 15, the chart 1500 displays a modified range for the heart rate values defined by upper and lower limits 1506, 1508. The modified range can be displayed in response to selection of the treatment event 1510 in accordance with the examples described above. In examples where the chart 1500 displays a plurality of treatment events, each treatment event is selectable to view a modified range of heart rate values based on the expected effect of the selected treatment event, and its interaction with one or more prior treatment events.

In some examples, the chart 1500 can display a modified range for the heart rate values without requiring a selection of the treatment event 1510. In such examples, the modified range for the heart rate values defined by the upper and lower limits 1506, 1508 is displayed on the chart 1500 regardless of whether or not a clinician has selected the treatment event 1510.

The upper and lower limits 1506, 1508 of the modified range are displayed as curves that show an expected increase in the heart rate values based on the side effect of the of the albumin infusion followed by an expected decrease once the side effect of the albumin infusion begins to wear off. Accordingly, the upper limit 1506 of the modified range is higher than the upper limit 1502 of the normal range, and the lower limit 1508 of the modified range is higher than the lower limit 1504 of the normal range. The modified range between the upper and lower limits 1502, 1504 is overlayed on the heart rate values in a third shade of color.

As shown in FIG. 15, the first, second, and third shades of color when overlayed on the heart rate values are overlapped with one another, and can be used to provide intuitive information that improves the operation of the monitor device 104. As an example, the first shade of color for the normal range is gray and the third shade of color of the modified range is a color (e.g., red, green, blue, yellow, etc.) such that the portion in the chart 1500 where the modified range is overlapped by the normal range is a darker shade of the color, and the portion in the chart 1500 where the modified range is not overlapped by the normal range is a lighter or brighter shade of the color. This can help visualize expected targeted effects or side effects of treatment events on the physiological data values measured by the physiological sensor 108. Advantageously, the display of treatment events 1510 and overlapping normal and modified ranges can help a clinician to decide whether to respond to an alarm or adjust an alarm setting, determine whether a medical intervention is needed, and/or initiate the crisis alarm mode 142.

In some alternative examples, only the modified range defined by the upper and lower limits 1506, 1508 is displayed over the trendline of heart rate values when the treatment event 1510 is selected, such that the normal range defined the upper and lower limits 1502, 1504 is hidden. Such examples can prevent over-crowding of information displayed on the chart 1500.

As described above, the alarm application 126 and visualization application 128 can operate together on the monitor device 104 such that the chart 1500 can be displayed while the monitor device 104 operates under the normal alarm mode 140 and the crisis alarm mode 142. In the example shown in FIG. 15, the heart rate values are classified as abnormal when they exceed the upper limit 1502 of the normal range of heart rate values regardless of whether they are below the upper limit 1506 of the modified range of heart rate values. In such an example, an alarm is triggered by the alarm application 126 when the heart rate values exceed the upper limit 1502 of the normal range, but are below the upper limit 1506 of the modified range.

In an alternative example, the heart rate values are classified as abnormal only when they exceed the upper limit 1506 of the modified range. In some instances, an alarm is triggered by the alarm application 126 whenever the heart rate values exceed the upper limit 1506 of the modified range of heart rate values. In other instances, an alarm is triggered when the heart rate values are a predetermined distance beyond the upper limit 1506 of the modified range.

As another example, the upper and lower limits 1502, 1504 of the normal range of heart rate values can self-adjust when the alarm application 126 operates under the crisis alarm mode 142. Also, the upper and lower limits 1506, 1508 of the modified range of heart rate values can self-adjust when the alarm application 126 operates under the crisis alarm mode 142.

The various embodiments described above are provided by way of illustration only and should not be construed to be limiting in any way. Various modifications can be made to the embodiments described above without departing from the true spirit and scope of the disclosure.

What is claimed is:

1. A device for monitoring a physiological variable, comprising:
   at least one processing device; and
   a memory device storing instructions which, when executed by the at least one processing device, cause the device to:
   determine a starting value for a self-adjusting alarm limit based on an abnormal state of the physiological variable;
   receive a plurality of physiological data values from a physiological sensor during a time window;
   determine a new value for the self-adjusting alarm limit based on a calculation of the plurality of physiological data values received during the time window;
   when the new value for the self-adjusting alarm limit moves in a targeted direction, reset the self-adjusting alarm limit at the new value; and
   wherein a length of the time window is adjustable to adjust a sensitivity level of the self-adjusting alarm limit.

2. The device of claim 1, wherein the instructions further cause the device to:
   when the new value for the self-adjusting alarm limit moves in a direction opposite of the targeted direction, trigger an alarm.

3. The device of claim 1, wherein when the self-adjusting alarm limit is an upper alarm limit, the targeted direction is a decreasing targeted direction; and wherein when the self-adjusting alarm limit is a lower alarm limit, the targeted direction is an increasing targeted direction.

4. The device of claim 1, wherein the new value for the self-adjusting alarm limit is based on a percentile calculated from the physiological data values received during the time window.

5. The device of claim 1, wherein the new value for the self-adjusting alarm limit is based on a standard deviation of the physiological data values received during the time window.

6. The device of claim 1, wherein the instructions further cause the device to:
   determine an updated value for the self-adjusting alarm limit from physiological data values received during a subsequent time window;
   when the updated value for the self-adjusting alarm limit moves in the targeted direction, reset the self-adjusting alarm limit at the updated value; and
   when the updated value for the self-adjusting alarm limit moves in a direction opposite of the targeted direction, trigger an alarm.

7. The device of claim 6, wherein the instructions further cause the device to:
   determine a plurality of updated values for resetting the self-adjusting alarm limit during successive time windows until one or more exit criteria are satisfied.

8. The device of claim 7, wherein the one or more exit criteria include a target value within a normal range of the physiological variable.

9. The device of claim 7, wherein the one or more exit criteria include a time limit.

10. The device of claim 1, wherein the instructions further cause the device to:
    receive artifact data;
    determine whether the artifact data exceeds a predetermined threshold amount; and
    when the artifact data exceeds the predetermined threshold amount, exclude the physiological data values affected by the artifact data when determining the new value for the self-adjusting alarm limit, or alter a display of the physiological data values on a display device.

11. The device of claim 1, wherein the instructions further cause the device to:
    receive a treatment event;
    determine an expected effect of the treatment event on the physiological data values; and
    alter a display of the physiological data values based on the expected effect.

12. The device of claim 11, wherein the physiological data values are displayed to include the treatment event and a modified range overlayed on the physiological data values, wherein the modified range has upper and lower limits based on the expected effect.

13. The device of claim 12, wherein the upper and lower limits of the modified range are curves that show expected increases and decreases in the physiological data values.

14. The device of claim 13, wherein the modified range is shaded differently based on where the modified range overlaps a normal range of the physiological data values.

15. A method of continuous physiological monitoring, comprising:
    determining a starting value for a self-adjusting alarm limit based on an abnormal state of a physiological variable;
    receiving a plurality of physiological data values from a physiological sensor during a time window;
    determining a new value for the self-adjusting alarm limit based on a calculation of the plurality of physiological data values received during the time window;
    resetting the self-adjusting alarm limit at the new value when the new value for the self-adjusting alarm limit moves in a targeted direction;
    adjusting a length of the time window to adjust a sensitivity level of the self-adjusting alarm limit; and
    triggering an alarm when the new value for the self-adjusting alarm limit moves in a direction opposite of the targeted direction.

16. The method of claim 15, further comprising:
determining an updated value for the self-adjusting alarm limit from physiological data values received during a second time window;
resetting the self-adjusting alarm limit at the updated value when the updated value for the self-adjusting alarm limit moves in the targeted direction; and
triggering the alarm when the updated value for the self-adjusting alarm limit moves in a direction opposite of the targeted direction.

17. The method of claim 15, further comprising:
receiving artifact data;
determining whether the artifact data exceeds a predetermined threshold amount; and
excluding the physiological data values affected by the artifact data when determining the new value for the self-adjusting alarm limit, or altering a display of the physiological data values when the artifact data exceeds the predetermined threshold amount.

18. The method of claim 15, further comprising:
receiving a treatment event;
determining an expected effect on the physiological data values based on the treatment event, the expected effect being a targeted effect or a side effect; and
altering a display of the physiological data values based on the expected effect.

19. The method of claim 18, further comprising:
displaying the treatment event overlayed on the physiological data values; and
displaying a modified range overlayed on the physiological data values, the modified range having upper and lower limits based on the expected effect of the treatment event.

* * * * *